US012810430B2

(12) United States Patent
Madabhushi et al.

(10) Patent No.: US 12,810,430 B2
(45) Date of Patent: Nov. 24, 2026

(54) PREDICTION OF CARDIAC REJECTION VIA MACHINE LEARNING DERIVED FEATURES FROM DIGITAL ENDOMYOCARDIAL BIOPSY IMAGES

(71) Applicants: Case Western Reserve University, Cleveland, OH (US); The Trustees of the University of Pennsylvania, Philadelphia, PA (US)

(72) Inventors: Anant Madabhushi, Shaker Heights, OH (US); Sara Arabyarmohammadi, Shaker Heights, OH (US); Cai Yuan, Pendleton, SC (US); Eliot G. Peyster, Philadelphia, PA (US); Kenneth B. Margulies, Villanova, PA (US); Michael D. Feldman, Wilmington, DE (US); Priti Lal, Ellicott City, MD (US)

(73) Assignees: Case Western Reserve University, Cleveland, OH (US); The Trustees of the University of Pennsylvania, Philadelphia, PA (US)

( * ) Notice: Subject to any disclaimer, the term of this patent is extended or adjusted under 35 U.S.C. 154(b) by 827 days.

(21) Appl. No.: 17/982,147

(22) Filed: Nov. 7, 2022

(65) Prior Publication Data

US 2023/0148068 A1 May 11, 2023

Related U.S. Application Data

(60) Provisional application No. 63/276,750, filed on Nov. 8, 2021.

(51) Int. Cl.
*G06T 7/00* (2017.01)
*A61B 5/00* (2006.01)

(52) U.S. Cl.
CPC ............ *G06T 7/0014* (2013.01); *A61B 5/413* (2013.01); *G06T 2207/20081* (2013.01); *G06T 2207/20084* (2013.01); *G06T 2207/30048* (2013.01)

(58) Field of Classification Search
CPC ......... G06T 7/0014; G06T 2207/20081; G06T 2207/20084; G06T 2207/30048; A61B 5/413
See application file for complete search history.

(56) References Cited

U.S. PATENT DOCUMENTS

2019/0279359 A1* 9/2019 Madabhushi ........ G06V 10/763

OTHER PUBLICATIONS

Nirschl, Jeffrey J et al. "A Deep-Learning Classifier Identifies Patients with Clinical Heart Failure Using Whole-Slide Images of H&E Tissue." PloS one 13.4 (2018): e0192726. Web. (Year: 2018).*

(Continued)

*Primary Examiner* — John R Wallace
(74) *Attorney, Agent, or Firm* — Eschweiler & Potashnik, LLC

(57) ABSTRACT

The present disclosure in some embodiments relates to a non-transitory computer-readable medium storing computer-executable instructions that, when executed, cause a processor to perform operations, including obtaining one or more digitized endomyocardial biopsy (EMB) images from a patient having had a heart transplant; extracting a plurality of histological features from the one or more digitized EMB images; and applying a machine learning predictive model to operate on the plurality of histological features to generate a prediction for the patient. The prediction includes a grade or a clinical trajectory associated with the patient.

11 Claims, 12 Drawing Sheets

(56) References Cited

OTHER PUBLICATIONS

Peyster, Eliot G et al. "In Situ Immune Profiling of Heart Transplant Biopsies Improves Diagnostic Accuracy and Rejection Risk Stratification." JACC. Basic to translational science 5.4 (2020): 328-340. Web. (Year: 2020).*

* cited by examiner

PREDICTION OF CARDIAC REJECTION VIA MACHINE LEARNING DERIVED FEATURES FROM DIGITAL ENDOMYOCARDIAL BIOPSY IMAGES

REFERENCE TO RELATED APPLICATION

This application claims the benefit of U.S. Provisional Application No. 63/276,750, filed on Nov. 8, 2021, the contents of which are hereby incorporated by reference in their entirety.

FEDERAL FUNDING NOTICE

This invention was made with government support under HL151277 and HL158071 awarded by the National Institutes of Health. The government has certain rights in the invention.

BACKGROUND

Transplantation is the act of removing an organ from one person (i.e., a donor) and surgically placing the organ into another person (i.e., a recipient). Transplantation is used as treatment for different medical conditions. For example, heart transplantation may be performed because a recipient's heart has been damaged and/or is unable to continue to pump blood thorough a person's body.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Figure 1:
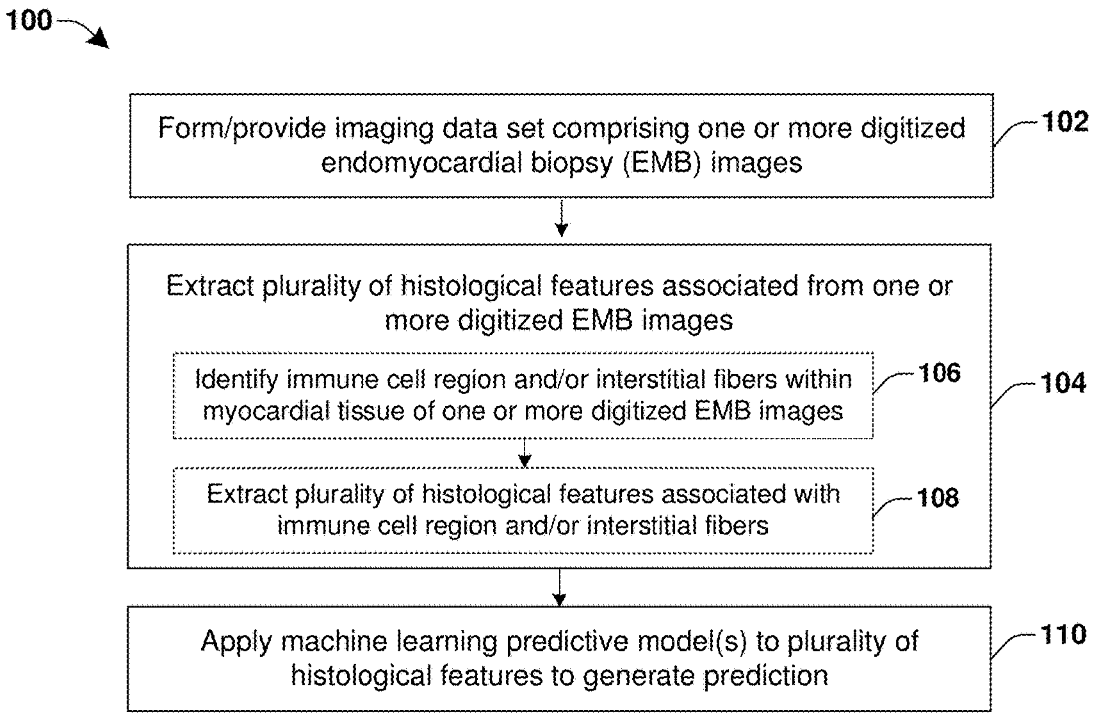
FIG. 1 illustrates some embodiments of a method of determining a prediction for a transplant recipient based on histological features extracted from one or more digitized endomyocardial biopsy (EMB) images.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

A person's immune system typically protects the person from harmful foreign substances (e.g., germs, bacteria, etc.). When a recipient receives an organ from another person, the recipient's immune system may recognize the transplanted organ as a foreign substance. This is because the transplanted organ has proteins called antigens coating its surface. In some cases, as soon as these antigens enter the recipient's body, the immune system may recognize them as belonging to a harmful foreign substance. Therefore, the recipient may reject the transplanted organ, leading to graft failure. In heart transplant patients, cardiac allograft rejection is a significant concern for between approximately 20% and approximately 40% of transplant recipients during the first-year post-transplant.

An endomyocardial biopsy (EMB) is a procedure that is often used for routine surveillance of heart transplant patient. An EMB is a procedure that obtains small amounts of myocardial tissue for diagnosis of rejection in a transplanted heart. An EMB can identify graft rejection before dysfunction occurs as a consequence of the rejection. Typically, the myocardial tissue is digitized to form EMB images, which are subsequently used to form grades (e.g., ISHLT (international society for heart and lung transplantation) rejection grades) describing a rejection. The grades range from mild rejection (e.g., grades 0R and/or 1R) to severe rejection (e.g., grades 2R and/or 3R).

However, it has been appreciated that the grades often do not accurately describe how a patient is really doing (e.g., a clinical outcome). For example, sometimes a patient receiving a low grade (e.g., grade 0R or 1R) based upon an EMB image may have a poor clinical outcome, while a patient receiving a high grade (e.g., grade 2R or 3R) based on an EMB image may have a good clinical outcome. Furthermore, inter-pathologist agreement is often poor, thereby causing uncertainty in results and exacerbating this grading problem. Such uncertainty and discordance can lead to misguided treatment that can negatively impact patients.

Artificial intelligence (AI) classifiers may be used to try to alleviate some of these problems. However, such models so far have failed to achieve good agreement with pathologists. Moreover, deep learning models provide little insight into a prediction due to their limited interpretability (e.g., 'black box' operation). This limited insight into a prediction makes it difficult to apply the results of such deep learning models to clinical settings.

Accordingly, the present disclosure relates to method that utilizes a machine learning pipeline to operate upon digitized EMB images to generate a prediction that is able to provide for good agreement with ISHLT grades and/or with clinical trajectories. In some embodiments, the method comprises obtaining one or more digitized endomyocardial biopsy (EMB) images from one or more patients having received heart transplants. A plurality of histological features are extracted from the one or more digitized EMB features. In some embodiments, the plurality of histological features may be extracted from immune cell regions and/or interstitial fibers. A machine learning predictive model is operated to use the plurality of histological features to generate one or more predictions that are indicative of grading and/or clinical outcomes of a patient associated with the one or more digitized EMB images. By utilizing a machine learning predictive model that operates on histological features specifically chosen to correspond to an outcome (e.g., extracted from immune cell regions and/or interstitial fibers), the model can provide for a high accuracy of ISHLT grades and/or clinical trajectories that can improve clinical decisions (e.g., treatment decisions) regarding a patient.

FIG. 1 illustrates some embodiments of a method 100 of determining a prediction for a transplant recipient based on histological features extracted from one or more digitized endomyocardial biopsy (EMB) images.

While the disclosed methods (e.g., methods 100, 500, and 1400) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At act 102, an imaging data set comprising one or more digitized endomyocardial biopsy (EMB) images is formed and/or provided. The one or more digitized EMB images are from one or more patients that have received a heart transplant. In some embodiments, the one or more patients may comprise hundreds or thousands of patients respectively having at least one EMB image within the imaging data set.

At act 104, a plurality of histological features are extracted from the one or more digitized EMB images. In some embodiments, the plurality of histological features are extracted from every one of the one or more EMB images (e.g., from the hundreds or thousands of EMB images). In some embodiments, the plurality of histological features may be extracted from the one or more digitized EMB images according to acts 106-108.

At act 106, immune cell regions (e.g., lymphocyte clusters and/or foci) and/or interstitial fibers (e.g., interstitium) are identified within myocardial tissue of the one or more digitized EMB images.

At act 108, a plurality of histological features associated with the immune cell regions and/or interstitial fibers are extracted.

At act 110, one or more machine learning predictive models are applied to the plurality of histological features to generate one or more predictions. In some embodiments, the one or more machine learning predictive models may be configured to generate a grade of a patient (e.g., a ISHLT grade). In other embodiments, the one or more machine learning predictive models may be configured to generate a clinical trajectory of a patient (e.g., a silent clinical trajectory of a patient that will exhibit few or no symptoms or an evident clinical trajectory of a patient that will exhibit symptoms).

It has been appreciated that applying the disclosed machine learning predictive models to the plurality of histological features provides for a prediction that has a higher accuracy, along with a better interpretability and/or transparency, than deep learning models applied to pathological features. This is at least in part because the disclosed machine learning model does not blindly apply machine learning to form a prediction (e.g., as in the case of the 'black box' approach of deep learning), but instead the plurality of histological features used by the machine learning predictive model can be selectively chosen (e.g., from immune cell regions and/or interstitial fibers) to have a higher relevance to the prediction (e.g., to have an explainable connection to the prediction). Furthermore, the disclosed machine learning predictive models can consistently achieve accurate predictions, thereby avoiding the inconsistencies in grading that may be present between human pathologist. The predictions can provide practitioners an alternative metric to human grading that may be able to identify patients having a high likelihood of transplant rejection, thereby allowing practitioners a better ability to treat transplant rejection and prevent cardiac dysfunction and/or patient death.

Figure 2:
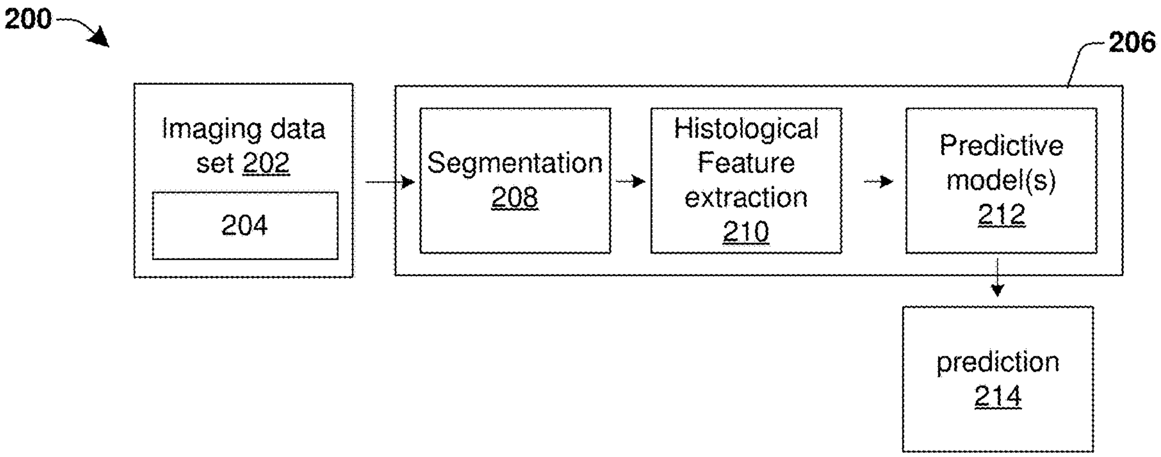
FIG. 2 illustrates some embodiments of a block diagram of a machine learning pipeline configured to determine a prediction for a transplant recipient based on histological features extracted from one or more digitized EMB images.

FIG. 2 illustrates some embodiments of a block diagram 200 of a machine learning pipeline configured to determine a prediction for a transplant recipient based on histological features extracted from one or more digitized EMB images.

As shown in the block diagram 200, an imaging data set 202 is formed and/or provided. The imaging data set 202 comprises one or more digitized EMB images 204. In some embodiments, the one or more digitized EMB images 204 respectively include an image of myocardial tissue taken from the heart of a patient that has received a heart transplant. In some embodiments, the one or more digitized EMB images 204 may comprise digitized hematoxylin and eosin (H&E) stain transplant EMB histology slides.

The one or more digitized EMB images 204 are provided to a machine learning pipeline 206 that is configured to apply one or more machine learning predictive models to histological features extracted from the plurality of digitized EMB images 204 to determine a prediction 214 of a patient having had a heart transplant. In some embodiments, the machine learning pipeline 206 comprises a segmentation stage 208, a histological feature extraction stage 210, and a machine learning predictive model stage 212.

The segmentation stage 208 is configured to segment the one or more digitized EMB images 204. In some embodiments, the segmentation stage 208 may be configured to identify immune cell regions (e.g., lymphocytes, lymphocytes foci, lymphocyte clusters, or the like) within the one or more digitized EMB images 204. In some such embodiments, the segmentation stage 208 may be configured to utilize a stain color deconvolution algorithm to detect the immune cell regions (e.g., lymphocytes, lymphocytes foci, lymphocyte clusters, or the like) across tissue specimens. In some embodiments, the segmentation stage 208 may be configured to identify interstitial fibers (e.g., interstitial collagen fibers, interstitial stromal fibers, or the like) within the one or more digitized EMB images 204.

The histological feature extraction stage 210 is configured to extract a plurality of histological features from the segmented images. In some embodiments, the histological feature extraction stage 210 may extract the plurality of histological features from immune cell regions and/or interstitial fibers within respective ones of the one or more digitized EMB images 204. In some embodiments, the plurality of histological features may comprise one or more of a number of lymphocytes and/or lymphocyte foci, a spatial arrangement of lymphocytes and/or lymphocyte foci, a shape of interstitial fibers, a density of interstitial fibers, and/or an orientation of interstitial fibers. In other embodiments, the plurality of histological features may comprise features quantifying a number of lymphocyte foci in different tissue compartments (e.g., in a myocardial compartment, an endocardial compartment, or the like), size or density statistics for lymphocyte clusters, and/or spatial or edge interactions of lymphocyte clusters and foci. In yet other embodiments, the plurality of histological features may comprise endocardial interstitial fibers solidity (which quantifies an amount of convexity of interstitial fibers in an endocardial region), endocardial interstitial fibers density (which captures a density of interstitial fibers in the endocardial region), lymphocyte foci count (which captures a sum of proximity graphs that group lymphocytic clusters), lymphocyte area ratio (which captures an area covered by all lymphocyte nuclei divided by WSI area), lymphocyte foci area ratio (which characterizes an area covered by lymphocyte foci in WSI), and non-myocardium lymphocyte foci area ratio (which reflects an area covered by lymphocyte foci divided by non-myocardium regions area).

The machine learning predictive model stage 212 is configured to apply and/or generate one or more machine learning predictive models that utilize the plurality of histological features to generate a prediction 214 of a patient. In some embodiments, the one or more machine learning predictive models may be configured to provide a binary classification. For example, the one or more machine learning predictive models may be configured to provide a first output that denotes a low grade (e.g., 0R, 1R) or a second output that denotes a high grade (e.g., 2R or 3R). In other embodiments, the one or more machine learning predictive models may be configured to provide a 4-grade classification (e.g., having outputs corresponding to 0R, 1R, 2R, or 3R). In yet other embodiments, the one or more machine learning predictive models may be configured to generate an output that is indicative of a clinical trajectory (e.g., a ‘0’ indicating a silent clinical trajectory of a patient will exhibit few or no symptoms or a ‘1’ indicating an evident clinical trajectory of a patient that will exhibit symptoms).

In various embodiments, the one or more machine learning predictive models of the machine learning predictive model stage 212 may comprise a linear classifier. For example, in some embodiments the one or more machine learning predictive models of the machine learning predictive model stage 212 may comprise a support vector machine (SVM) classification method. In other embodiments, the one or more machine learning predictive models of the machine learning predictive model stage 212 may utilize a linear discriminant analysis (LDA) classification method, a quadratic discriminant analysis (QDA) classification method, a Naive Bayes classification method, or the like.

It will be appreciated that the disclosed methods and/or block diagrams may be implemented as computer-executable instructions, in some embodiments. Thus, in one example, a computer-readable storage device (e.g., a non-transitory computer-readable medium) may store computer executable instructions that if executed by a machine (e.g., computer, processor) cause the machine to perform the disclosed methods and/or block diagrams. While executable instructions associated with the disclosed methods and/or block diagrams are described as being stored on a computer-readable storage device, it is to be appreciated that executable instructions associated with other example disclosed methods and/or block diagrams described or claimed herein may also be stored on a computer-readable storage device.

Figure 3:
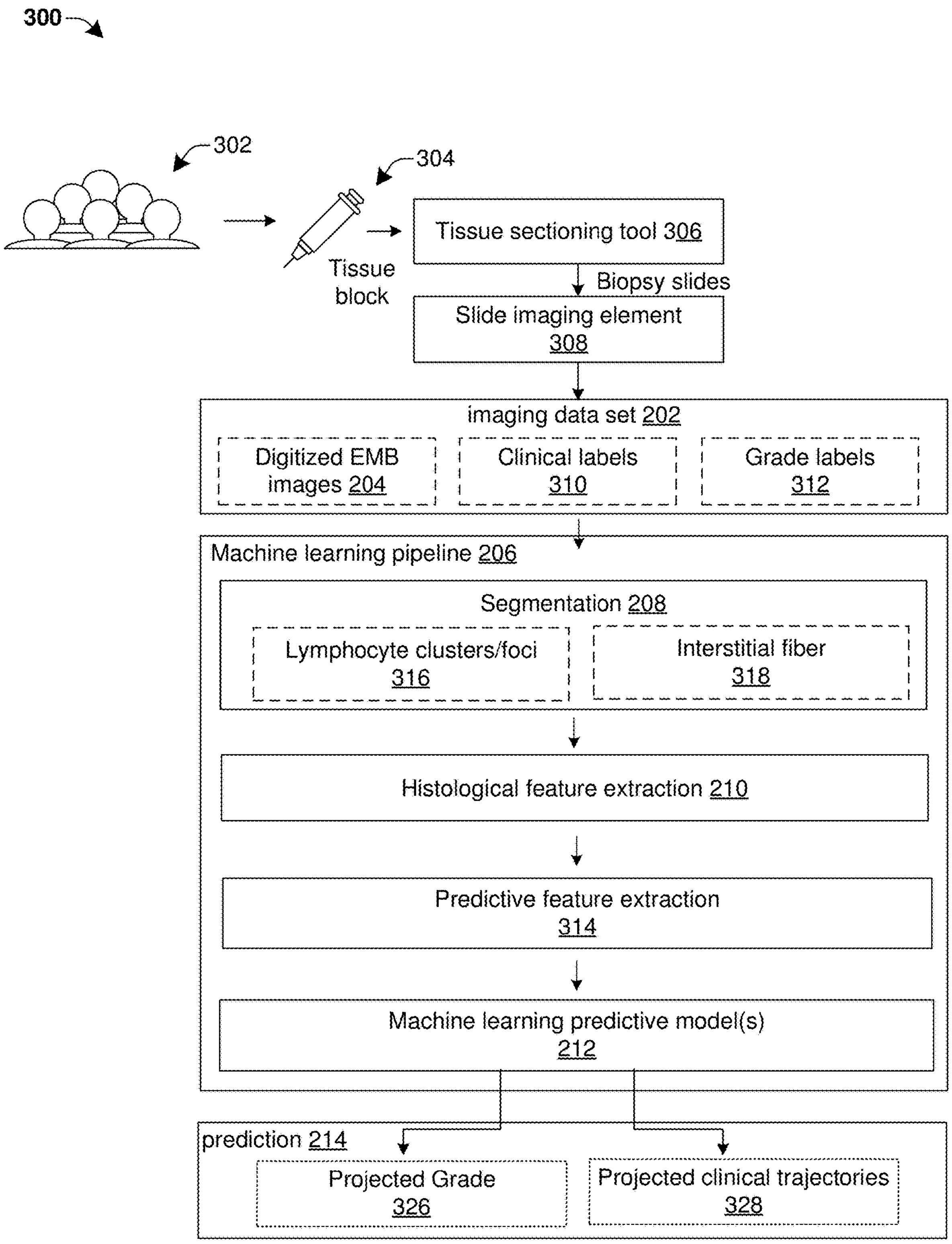
FIG. 3 illustrates some embodiments of a block diagram corresponding to a method and/or apparatus configured to determine a prediction for a transplant recipient based on histological features extracted from digitized EMB images.

FIG. 3 illustrates some embodiments of a block diagram 300 corresponding to a method and/or apparatus for determining a prediction of a transplant recipient based on histological features extracted from digitized EMB images.

As shown in the block diagram 300, an imaging data set 202 comprising one or more digitized EMB images 204 is formed and/or provided. The one or more digitized EMB images 204 are images that are derived from tissue samples taken from myocardial tissue of one or more patients 302 after a heart transplantation has occurred. In some embodiments, the one or more digitized EMB images 204 may be obtained by inserting a catheter 304 into a patient's heart to obtain a tissue sample (e.g., a tissue block). The tissue sample is the provided to a tissue sectioning tool 306 that is configured to slice the tissue into thin slices that are placed on transparent slides (e.g., glass slides) to generate biopsy slides. The biopsy slides are subsequently provided to a slide imaging element 308 (e.g., a photodetector) configured to convert the biopsy slides to the one or more digitized EMB images 204.

In some embodiments, the one or more digitized EMB images 204 may be subjected to quality control (QC) assessments. For example, digitized EMB images that contain major process and/or staining artifacts (e.g., folds or other lines, overstains, blurriness, black spots, or the like) may be excluded from the imaging data set 202. In some embodiments, the quality control assessments may be performed by pathology analysis software configured to identify artifacts and/or measure slide quality. For example, the quality control assessments may be performed by pathology analysis software configured use a combination of image metrics (e.g., color/intensity/contrast histograms), features (e.g., edge detectors), and/or supervised classifiers (e.g., pen detection) to exclude digitized EMB images with low resolution and excessive artifacts from the imaging data set 202.

In some embodiments, the imaging data set 202 may further comprise clinical labels 310 associated with the one or more digitized EMB images 204. The clinical labels 310 are labels that describe how a patient associated with respective ones of the one or more digitized EMB images 204 progresses clinically over time. For example, the clinical labels 310 may describe a patient's survival over time (e.g., a 5-year survival). In some embodiments, the imaging data set 202 may further comprise grade labels 312 associated with the one or more digitized EMB images 204. For example, the grade labels 312 may comprise ISHLT grades (e.g., 0R, 1R, 2R, or 3R).

The one or more digitized EMB images 204 are provided to a machine learning pipeline 206 configured to generate a prediction 214 for a patient based upon a plurality of histological features extracted from the one or more digitized EMB images 204. In some embodiments, the machine learning pipeline 206 comprises a segmentation stage 208, a histological feature extraction stage 210, a predictive feature extraction stage 314, and a machine learning predictive model stage 212.

The segmentation stage 208 is configured to generate segmented images that identify one or more regions of interest within the one or more digitized EMB images 204. In some embodiments, the one or more regions of interest may comprise immune cell regions (e.g., lymphocytes, lymphocyte clusters/foci, or the like) and/or interstitial fibers within the one or more digitized EMB images 204. In some embodiments, the segmentation stage 208 may be configured to use a stain color deconvolution algorithm to detect lymphocytes and/or lymphocyte clusters/foci 316 across tissue specimens. In such embodiments, the color densities and surface areas stained with a specific color are determined. In some embodiments, lymphocyte clusters/foci are first identified by performing disc-dilation and area thresholding and then lymphocyte foci are identified by aggregating the clusters using proximity graph thresholding with individual lymphocytes acting as vertices and edges of the clusters within and between clusters being determined using thresholding of Euclidean distances.

In some additional embodiments, the one or more regions of interest may comprise interstitial fibers 318. In some embodiments, the segmentation stage 208 may identify interstitial fibers 318 within endocardial, interstitial, and myocardial regions. In some embodiments, the segmentation stage 208 may use a local difference local binary pattern (LD-LBP) operator combined with OTSU algorithm to detect the interstitial fibers. The LD-LBP operator is a texture operator that labels an image's pixels by thresholding a magnitude relationship between a target pixel and neighboring pixels. The OTSU then separates pixels into two classes maximizing inter-class variance.

The histological feature extraction stage 210 is configured to extract a plurality of histological features from the segmented images. In some embodiments, the plurality of histological features may comprise features related to interstitial fibers (e.g., collagen fibers, stromal fibers, or the like). For example, the features may describe a shape, size, density, orientation, distribution patterns, and/or heterogeneity of an interstitial fiber (e.g., collagen fiber, stromal fibers, or the like). In some embodiments, the plurality of histological features may comprise features related to immune cells (e.g., lymphocyte clusters and/or foci). For example, the features may describe a spatial pattern and/or arrangement of immune cells, a lymphocyte number and/or arrangement, and/or other morphological features of an immune cell.

The histological features are provided to the predictive feature extraction stage 314. The predictive feature extraction stage 314 is configured to determine a subset of the histological features that are determinative of the prediction 214. In some embodiments, the subset of histological features may be identified using a Wilcoxon rank sum test that is configured to identify predictive features (e.g., features that are most closely associated with a given clinical result). For example, a Wilcoxon rank-sum test method may be applied across 500 iterations of 3-fold cross validation to identify the top features associated with clinically evident disease. In each iteration, a quadratic discriminant analysis model may be trained with the top 10 features on two folds of the data set using trajectory labels. The QDA model may be validated on a test set. In other embodiments, the subset of histological features may be identified using a t-test, a random forest algorithm, a minimum redundancy maximum relevance (mRMR) algorithm, or the like.

The subset of the histological features are provided to a machine learning predictive model stage 212. The machine learning predictive model stage 212 is configured to apply one or more machine learning predictive models to the subset of the histological features to determine the prediction 214. In some embodiments, the machine learning predictive model stage 212 may comprise a quadratic discriminant analysis (QDA) model. In some embodiments, the machine learning predictive model stage 212 may comprise a machine learning predictive model that is configured to provide a projected grade 326 associated with a patient. In some embodiments, the projected grade 326 may comprise a binary classification. For example, the machine learning predictive model may be configured to provide a first output that denotes a low grade (e.g., 0R or 1R) or a second output that denotes a high grade (e.g., 2R or 3R). In other embodiments, the projected grade 326 may comprise a 4-grade classification (e.g., outputs corresponding to 0R, 1R, 2R, or 3R). In some embodiments, the machine learning predictive model stage 212 may comprise a machine learning predictive model that is configured to provide a projected clinical trajectory 328 associated with a patient.

It has been appreciated that the subset of histological features that are indicative of a projected grade are different than the subset of histological features that are indicative of a projected clinical trajectory. Therefore, in different embodiments the predictive feature extraction stage 314 may be configured to identify different subsets of histological features depending on an associated machine learning predictive model and associated prediction. For example, the predictive feature extraction stage 314 may be configured to identify a first subset of histological features to generate a projected grade 326 and to identify a second subset of histological features to generate a projected clinical trajectory 328. In some embodiments, the first subset of histological features may be mainly based on immune cell architecture, while the second set of histological features may include interstitial fiber features.

Figure 4:
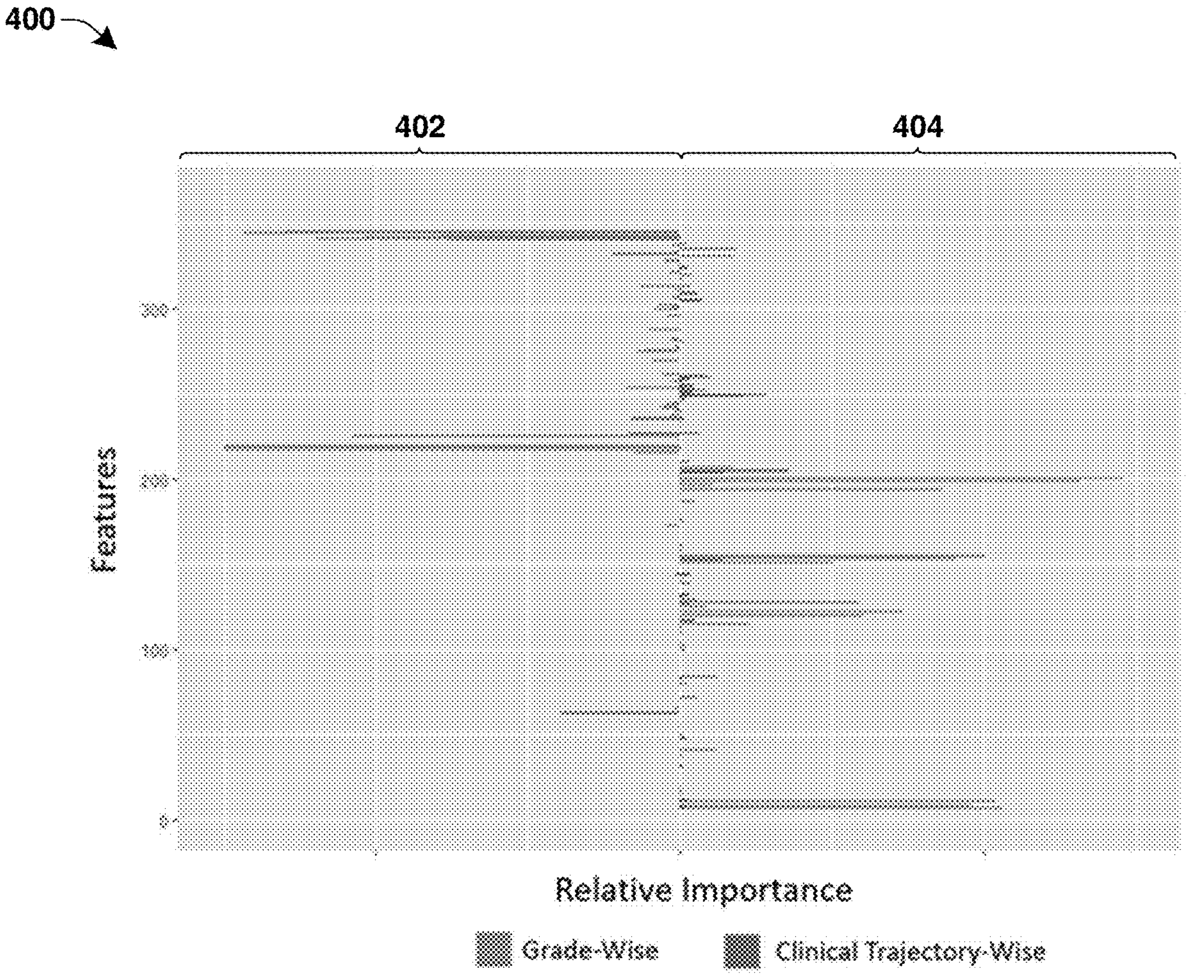
FIG. 4 illustrates some embodiments of a back-to-back bar chart comparing histological features used to generate predictions comprising grade projections and clinical trajectories.

FIG. 4 illustrates a back-to-back bar graph 400 comparing histological features used to generate predictions comprising grade projections and clinical trajectories.

As shown in graph 400, the importance of each feature for predicting ISHLT grade (e.g., "high-ISHLT" and "low-ISHLT" grade) is illustrated on the left 402. The importance of each feature for predicting clinical trajectory (e.g., "evident" versus "silent" clinical rejection) is illustrated on the right 404. In some embodiments, a clinically evident trajectory may be defined by an absolute left ventricular ejection fraction (LVEF) of less than or equal to approximately 40%, a proportional drop of LVEF of greater than or equal to approximately 25%, a cardiac index of less than 2.0 n $L/min/m^2$ plus use of inotropes, or the like.

The graph 400 shows a count of the features that were found to be important in a machine learning predictive model over a large number of cross-validation iterations. As shown in graph 400, the features that are the most important to accurately predict clinical trajectory (shown on right 404) are different than the features that are the most important to accurately predict ISHLT grades (shown on left 402). For example, the most important features for predicting clinical trajectories are predominantly interstitium-related features (e.g., features related to interstitial fibers), which are shown in graph 400 between features 0 and features 216. In contrast, the most important features for predicting ISHLT grades are mainly immune cell-related features (e.g., features related to lymphocytes, lymphocyte clusters, lymphocyte foci, etc.), which are shown in graph 400 between feature 217 and feature 364.

Therefore, graph 400 underscores a focus that the histological features used for predicting clinical trajectories are different than the histological features used for predicting grades. This difference may explain the discordance between conventional histology and rejection syndrome observed in clinical practice and highlights the ability of the disclosed machine learning pipeline to accurately predict clinical trajectories and explain rejection events. In other words, while grading (e.g., ISHLT grading schema) of digitized EMB images is not sufficient for predicting accurate rejection outcomes, the present disclosure provides for a more accurate prediction of such rejection outcomes by using different histological features than are used in grading.

Figure 5:
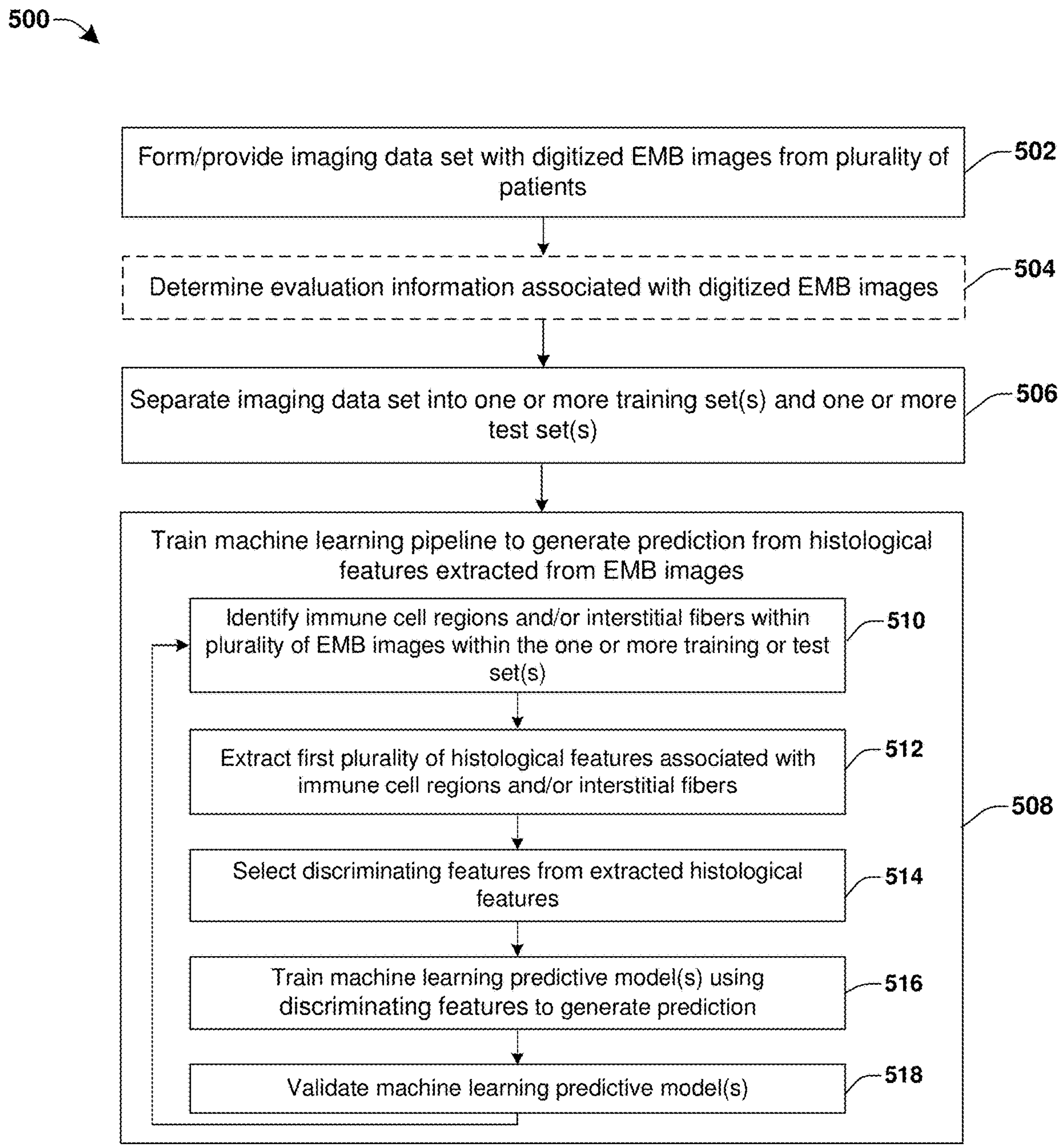
FIG. 5 illustrates some additional embodiments of a method of determining a prediction for a transplant recipient based on histological features extracted from digitized EMB images.

FIG. 5 illustrates some additional embodiments of a method 500 of determining a prediction for a transplant recipient based on histological features extracted from digitized EMB images.

At act 502, an imaging data set comprising a plurality of digitized EMB images is formed and/or provided. In some embodiments, the plurality of digitized EMB images may comprise images from a plurality of patients having various grades and/or clinical trajectories (e.g., evident low grade, silent low grade, evident high grade, and silent high grade) so enable subsequent formation of well-balanced training and/or test sets.

At act 504, evaluation information associated with the plurality of digitized EMB images may be determined, in some embodiments. In some embodiments, the evaluation information may comprise ISHLT grades (e.g., 0R, 1R, 2R, 3R) associated with the plurality of digitized EMB images. In some embodiments, the evaluation information may comprise trajectory labels (e.g., silent vs. evident) applied to the plurality of EMB images. The trajectory labels describe a clinical trajectory and/or outcome associated with respective ones of the plurality of digitized EMB images.

At act 506, the plurality of digitized EMB images within the imaging data set are separated into one or more training sets and one or more test sets. In some embodiments, the plurality of digitized EMB images may be broken into k folds of data.

At act 508, a machine learning pipeline is trained to generate a prediction from histological features extracted from the plurality of digitized EMB images. In some embodiments, the machine learning pipeline may operate on k−1 folds of data for training and the remaining 1 fold (e.g., the kth fold) of data for testing over a plurality of iterations (e.g., over 500 iterations). In some embodiments, each of the iterations may perform one or more operations of acts 510-518.

At act 510, immune cell regions (e.g., lymphocyte clusters and/or foci) and/or interstitial fibers (e.g., interstitial collagen fibers, interstitial stromal fibers, or the like) are identified within the plurality of digitized EMB images within the one or more training sets or the one or more test sets.

At act 512, a plurality of histological features associated with the immune cells (e.g., lymphocyte foci) and/or interstitial fibers are extracted.

At act 514, a subset of the plurality of histological features are selected as discriminating features. In some embodiments, the subset may comprise a set of the top 8 most discriminating features for determining a clinical trajectory associated with a digitized EMB image. In other embodiments, the subset may comprise a set of the top 15 most discriminating features for determining a grade associated with a digitized EMB image.

At act 516, one or more predictive machine learning models are trained using the discriminating features to generate a prediction.

At act 518, the one or more predictive machine learning models are validated. In some embodiments, the evaluation information associated with the plurality of digitized EMB images may be used to validate the one or more machine learning predictive models. For example, in some embodiments the first plurality of histological features may be mapped to a two-dimensional representation using a dimensional reduction technique (e.g., such as UMAP, t-SNE, or the like). In some embodiments, the disclosed machine learning pipeline may achieve an agreement of 86% with the trajectory label of record and an AUC of 0.81 for prediction of clinical trajectories. In some embodiments, the disclosed machine learning pipeline may achieve an accuracy of 0.61 and AUC of 0.41 in predicting silent vs. evident rejection trajectories once the machine learning model is trained based on low vs. high rejection grades only, and the machine learning pipeline may achieve a resulted in an accuracy of 0.72 and AUC of 0.54 in predicting low vs. high rejection grades once the machine learning model is trained based on trajectory labels only.

FIGS. 6-10 illustrate exemplary figures corresponding to a method (e.g., method 500) of training a machine learning predictive model to generate a prediction for a transplant recipient based on histological features extracted from digitized EMB images. Although FIGS. 6-10 are described in relation to the method 500, it will be appreciated that FIGS. 6-10 are not limited to such a method but instead may also stand alone and/or with other methods (e.g., method 100).

Figure 6:
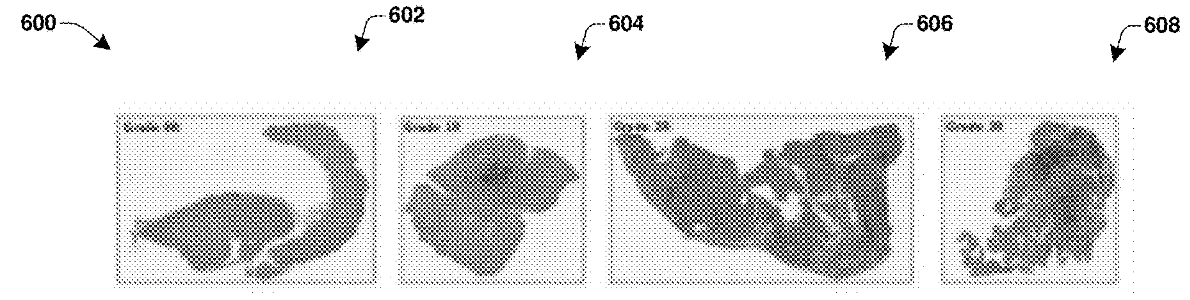
FIG. 6 illustrates some examples of digitized EMB images within a disclosed imaging data set.

FIG. 6 illustrates some examples of an imaging data set 600 comprising a plurality of digitized EMB images that may be disposed within an imaging data set.

In some embodiments, imaging data set 600 comprises a plurality of digitized EMB images 602-608 that respectively include an image of myocardial tissue taken from the heart of a patient that has received a heart transplant. In some embodiments, the plurality of digitized EMB images 602-608 may comprise digitized hematoxylin and eosin (H&E) stain transplant EMB histology slides. In some embodiments, the plurality of digitized EMB images 602-608 may be associated with different grades (e.g., ISHLT cellular rejection grades). For example, a first digitized EMB image 602 may be associated with grade 0R, a second digitized EMB image 604 may be associated with grade 1R, a third digitized EMB image 606 may be associated with grade 2R, and a fourth digitized EMB image 608 may be associated with grade 3R.

Figure 7:
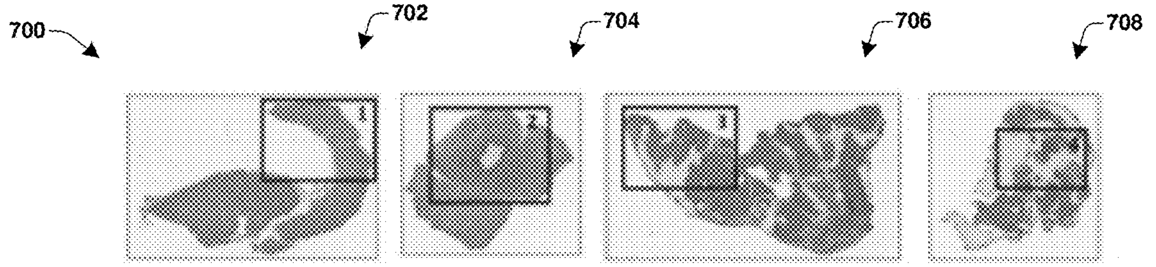
FIG. 7 illustrates some examples of digitized EMB images that are segmented to determine lymphocyte clusters and/or lymphocyte foci.

FIG. 7 illustrates some examples of digitized EMB images 700 that have been segmented to determine lymphocyte clusters and/or foci.

As shown in the digitized EMB images 700, a first digitized EMB image 702 having a 0R grade will have small lymphocyte clusters and/or foci. A second digitized EMB image 704 having a 1R grade will have larger lymphocyte clusters and/or foci. A third digitized EMB image 706 having a 2R grade will have yet larger lymphocyte clusters and/or foci. A fourth digitized EMB image 708 having a 3R grade will have large lymphocyte clusters and/or foci.

In some embodiments, the lymphocyte clusters and/or foci may be identified using a stain color deconvolution algorithm (e.g., to differentiate between a nuclei of a myocyte and a lymphocyte). In such embodiments, lymphocyte clusters may be identified by performing dilation (e.g., disc-dilation). The lymphocyte foci may be subsequently identified by aggregating the lymphocyte clusters. It has been appreciated that without aggregating the clusters, the number of lymphocyte foci can be overcounted thereby leading to a poor prediction from the disclosed machine learning pipeline. In some embodiments, the lymphocyte clusters may be aggregated using proximity graph thresholding with individual lymphocytes acting as vertices and edges of the lymphocytes being identified within and between clusters based on thresholding of Euclidean distances.

Once the lymphocyte clusters and/or foci have been identified they can be used to extract histological features from the digitized EMB images. For example, because lymphocyte foci denote an area at which immune cells may have damaged the myocardium, lymphocyte foci within a myocyte may be counted to determine a number of lymphocyte foci as a histological feature. In other embodiments, the area ratio of the lymphocyte foci may be determined to be a histological feature.

Figure 8:
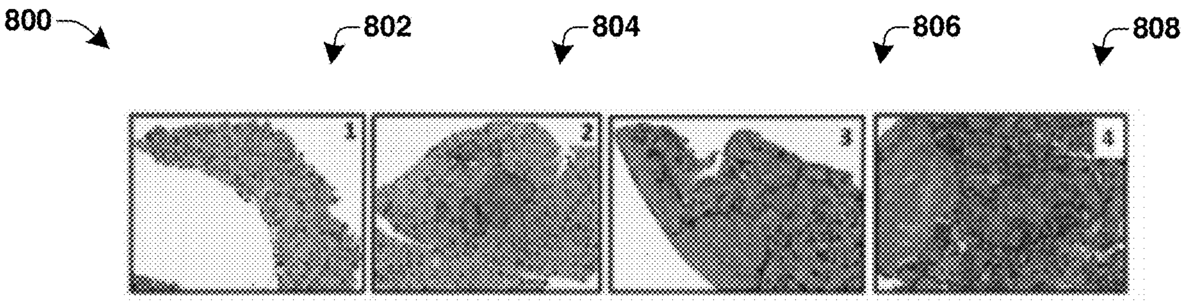
FIG. 8 illustrates some examples of digitized EMB images showing proximally situated lymphocytes.

FIG. 8 illustrates some examples of digitized images 800 showing proximally situated lymphocytes. The digitized images 800 of FIG. 8 correspond to the boxes shown in FIG. 7, so as to highlight zoomed-in areas of the digitized EMB images 700.

As shown in the digitized images 800, convex hulls of lymphocyte clusters comprising proximally situated lymphocytes are illustrated. The convex hulls are polygons that surround the lymphocyte clusters, to show that the lymphocyte clusters within the digitized images 800 associated with different grades have different shapes, different sizes, and/or different areas. For example, in the digitized images 802 and 804 associated with the 2R and 3R grades, lymphocyte clusters cover most of the tissue, while in the digitized images 806 and 808 associated with the 0R and 1R grades lymphocyte clusters are dispersed, small, and cover a small portion of the tissue sample.

Figure 9:
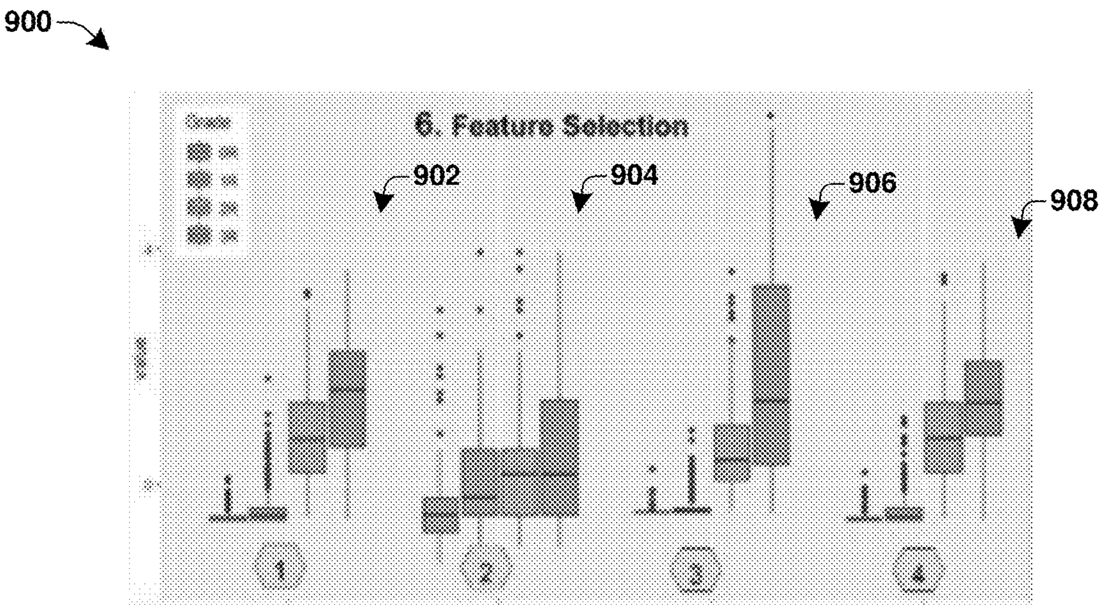
FIG. 9 illustrates some examples of bar graphs corresponding to a subset of determinative histological features selected from a plurality of histological features.

FIG. 9 illustrates example bar graphs 900 corresponding to a subset of determinative histological features selected from a plurality of histological features.

The bar graphs 900 illustrate an agreement of a feature with ISHLT rankings for different features and the selected features' power in differentiating between rejection grades. For example, a first feature is illustrated by graph 902. As shown in graph 902, the first feature has a relatively low contribution to a prediction for a grading 0R, and increasing contributions for prediction of gradings 1R to 3R. A second feature 904, a third feature 906, and a fourth feature 908 also have different contributions for different gradings. From the different contributions for different gradings, features can be identified that are most discriminative (e.g., important) to make a prediction. In various embodiments, the subset of top predictive histological features may be identified using a QDA model, a t-test, a random forest algorithm, a minimum redundancy maximum relevance (mRMR) algorithm, or the like.

Figure 10A:
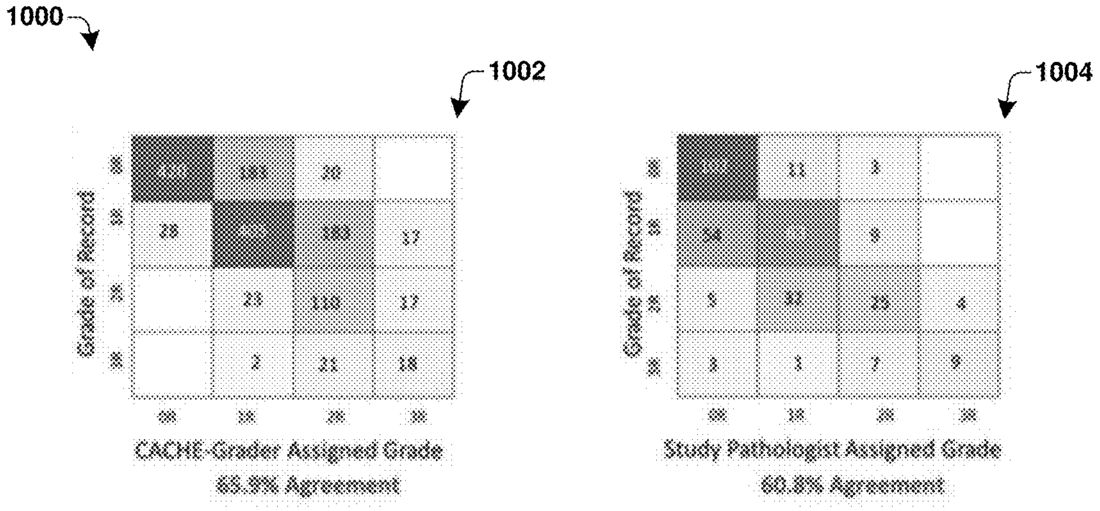
FIGS. 10A-10B illustrate some examples of validation techniques that validate the disclosed method and/or apparatus configured to determine a prediction for a transplant recipient.
Figure 10B:
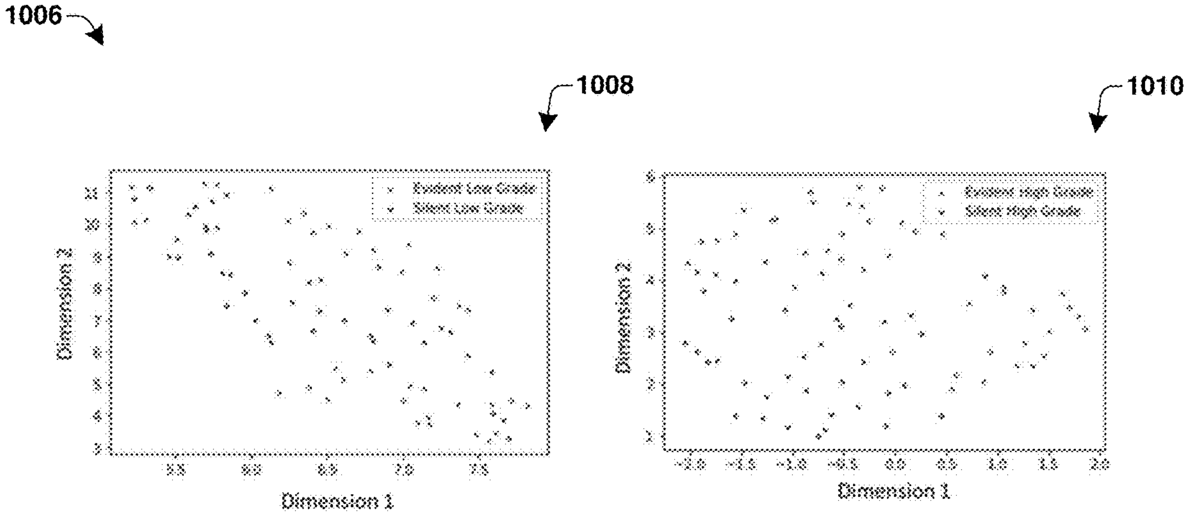

FIG. 10A illustrates confusion graphs showing agreement between the model output and the ISHLT grades of record. The graphs can be used to validate the model by determining agreement between the output of the model and grades of record associated with the different digitized EMB images. As shown in graph 1000, the disclosed machine learning pipeline is able to get an agreement of 65.9% with the grades of record. As shown in graph 1002, pathologist assigned grades were able to achieve an agreement of 60.8% with the grades of record (e.g., due to inter-pathologist disagreement). Comparison of graphs 1002 and 1004 illustrates that the disclosed machine learning pipeline is able to FIG. 10B illustrates graphs 1006 of an exemplary uniform manifold approximation and projection (UMAP) embeddings 1008-1010 configured to evaluate potential differential patterns between silent and evident groups with a common unsupervised approach. In some embodiments, the graphs 1006 may be generated using a fixed random number of cases (an arbitrary number preferably less than 50 to visualize the samples more clearly) from every category of silent low grades, evident low grades, silent high grades, and evident high grades. For example, 40 cases may be randomly from the four categories to form a balanced set of 160 cases. After removing highly correlated features (where the Pearson correlation coefficient of the two features was more than 0.85) from the collection of 364 immune cell and interstitial fiber features, the remaining features were embedded and then plotted into two dimensions using the UMAP to visualize the distribution of features among the silent versus evident groups. The graphs show that the disclosed machine learning pipeline is able to achieve discriminability for silent and evident low-grade patients.

Based on the graphs 1006, it has been appreciated that more lymphocyte foci and higher lymphocyte area ratio in evident trajectory patients compared to the silent patients. Furthermore, the values for stromal fiber solidity features are higher in evident low-grade patients compared to silent low-grade patients. For example, a density of interstitial fibers in the endocardial region on EMBs belonging to evident cases is less than the density in the same region on EMBs of silent patients. In other words, in silent cases, interstitial fibers accumulate more densely in the endocardial region. The interstitial fibers in the endocardial region were also observed to be more convex and rounder in silent patients compared to the evident patients.

Figure 11:
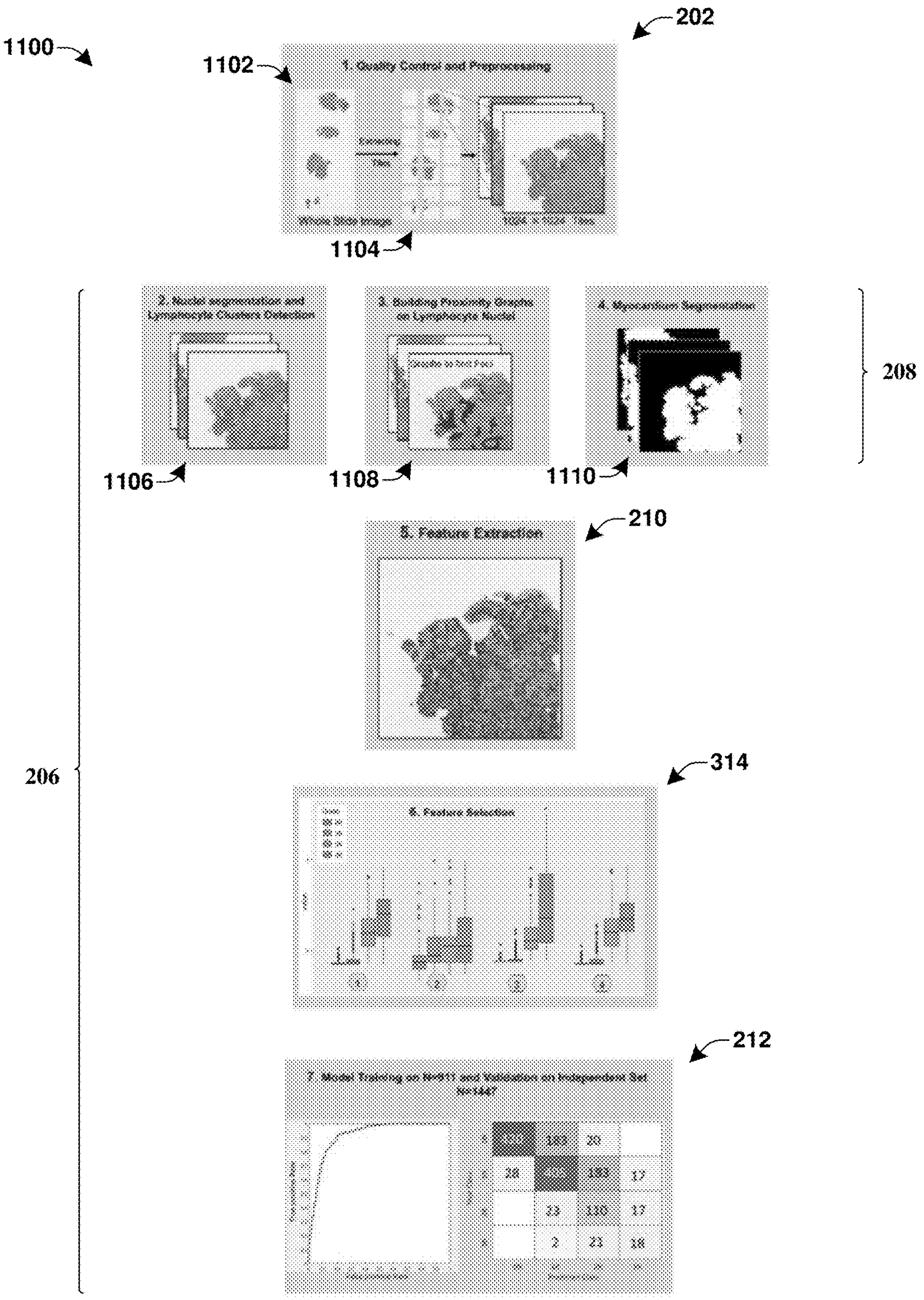
FIG. 11 illustrates some examples of a block diagram corresponding to a method and/or apparatus configured to determine a prediction for a transplant recipient based on histological features extracted from digitized EMB images.

FIG. 11 illustrates some embodiments of a block diagram 1100 corresponding to a method and/or apparatus configured to determine a prediction for a transplant recipient based on histological features extracted from a digitized EMB image.

As shown in block diagram 1100, an imaging data set 202 comprises a digitized EMB image 1102 that includes a whole slide image (WSI) of a digitized hematoxylin and eosin (H&E) stain transplant EMB histology slide. The digitized EMB image 1102 is divided into a plurality of tiles 1104 (e.g., patches). In some embodiments, the digitized EMB image 1102 may be divided into tiles 1104 that have a size of approximately 1024 pixels×1024 pixels, a size of approximately 4096 pixels×4096 pixels, or other similar values.

The plurality of tiles 1104 are provided to a machine learning pipeline 206. The machine learning pipeline 206 is configured to separately operate upon each of the plurality of tiles 1104. The machine learning pipeline 206 comprises a segmentation stage 208 that is configured to segment the plurality of tiles 1104, a histological feature extraction stage 210 that is configured to extract a plurality of histological features from the plurality of tiles 1104, a predictive feature extraction stage 314 configured to identify a set of determinative features from the plurality of histological features, and a machine learning predictive model stage 212 configured to apply the set of determinative features to a machine learning predictive model that is configured to generate a prediction.

In some embodiments, the segmentation stage 208 is configured to perform nuclei segmentation to identify immune cells regions and/or interstitial fibers. In some embodiments, the segmentation stage 208 may be configured to identify lymphocyte nuclei 1106 and to subsequently identify lymphocyte clusters 1108 by building proximity graphs based on the lymphocyte nuclei 1106.

The local neighborhood of a lymphocyte focus may be considered in determining histological features. For example, in some embodiments features of lymphocytes within myocytes may be considered while features of lymphocytes within endocardium may be discarded, since it has been appreciated that ignoring lymphocytes within endocardium may provide for a better agreement with ISHLT grading. In other embodiments, features encroaching upon myocyte borders may be considered in determining histological features. In such embodiments, myocyte and interstitium segmentations may be performed via K-means clustering, while more gross discrimination between myocardium vs. endocardium compartments may be achieved via a disc-dilation method. Spatial analysis of the locations and edge-interactions of lymphocyte clusters and/or foci may then be performed. For example, in some embodiments the plurality of histological features may comprise features that describe a relationship between the immune cells (e.g., lymphocytes) and a myocardium (e.g., a sum of an area covered by lymphocytes in lymphocyte clusters divided by an area of a myocardium). In such embodiments, the segmentation stage 208 may be further configured to perform myocardial segmentation 1110 to identify the myocardium within a tile.

In some embodiments, the segmentation stage 208 may be configured to respectively identify separate immune cell regions or separate interstitial fibers within the plurality of tiles 1104 and the histological feature extraction stage 210 may be configured to respectively generate a separate plurality of histological features associated with the separate immune cell regions or separate interstitial fibers. In such embodiments, statistical operations may be performed on each of the plurality of histological features across tiles relating to a patient to arrive at a patient level feature value. In some embodiments, the statistical features may comprise a mean, median, standard deviation, skewness or the like. In some embodiments, a histological feature vector may be determined from the plurality of histological features. The histological feature vector may relate to immune cell (e.g., lymphocyte) and/or interstitial fiber presentation characteristics.

Table 1 illustrates some examples of histological features that may be used by the disclosed machine learning pipeline to generate a prediction. It will be appreciated that the histological features shown in Table 1 are not exclusive but are merely examples of histological features that may be used by the disclosed machine learning pipeline.

TABLE 1

| No. | Histological feature name | Definition |
|---|---|---|
| 1 | StdDev of FociAreaRatio3 | Std of all FociAreaRatio3 on all tiles of the biopsy. FociAreaRatio3 is the sum of area covered by lymphocyte in lymphocyte clusters divide by area of myocardium in myocardium mask. |
| 2 | StdDev of MyoFociAreaRatio1 | Std of all MyoFociAreaRatio1 on all tiles of the biopsy. MyoFociAreaRatio1 is the ratio of foci area in myocardium divide by area of myocardium in myocardium mask. |
| 3 | StdDev of LymphAreaRatio8 | Std of all LymphAreaRatio8 on all tiles of the biopsy. LymphAreaRatio8 is the area covered by lymphocytes divided by area of myocardium. |
| 4 | Sum of MyoFociGraphCount | Sum of all MyoFociGraphCount on all tiles of the biopsy. MyoFociGraphCount is the count of proximal graphs build on the foci in the mask of the foci in myocardium. |
| 5 | Sum of FociCount | Sum of all FociCount on all tiles of the biopsy. FociCount is the first count of foci that was introduced in the first version before making graphs. |
| 6 | Sum of MyoFociCount | Sum of all MyoFociCount on all tiles of the biopsy. MyoFociCount is the number of components (foci) in the dilated version of the mask of foci in myocardium. |

TABLE 1-continued

| No. | Histological feature name | Definition |
|---|---|---|
| 7 | Sum of FociGraphCount | Sum of all FociGraphCount on all tiles of the biopsy. FociGraphCount is the count of proximal graphs build on the foci in lymphocyte cluster mask. |
| 8 | Sum of Myo_FociGraphCount | Sum of all Myo_FociGraphCount on all tiles of the biopsy. Myo_FociGraphCount is the FociGraphCount divide by area of myocardium in myocardium mask. |
| 9 | Sum of RawMyo_FociGraphCount | Sum of all RawMyo_FociGraphCount on all tiles of the biopsy. RawMyo_FociGraphCount is FociGraphCount divide by the Area of myocardium in raw myocardium masks before dialation. |
| 10 | Sum of Tissue_MyoFociGraphCount | Sum of all Tissue_MyoFociGraphCount on all tiles of the biopsy. Tissue_MyoFociGraphCount is the MyoFociGraphCount divide by the area where is covered by the tissue. |
| 11 | Sum of LymphFreeTissue_FociGraphCount | Sum of all LymphFreeTissue_FociGraphCount on all tiles of the biopsy. LymphFreeTissue_FociGraphCount is the FociGraphCount divided by Lymph_free_Tissue area. |
| 12 | Sum of Title_MyoFociGraphCount | Sum of all Tile_MyoFociGraphCount on all tiles of the biopsy. Tile_MyoFociGraphCount is the MyoFociGraphCount divided by the whole tile area. |
| 13 | Sum of Lymph_MyoFociGraphCount | Sum of all Lymph_MyoFociGraphCount on all tiles of the biopsy. Lymph_MyoFociGraphCount is the MyoFociGraphCount divided by the area covered by all lymphocytes |
| 14 | Average of LymphAreaRatio1 | Average of all LymphAreaRatio1 on all tiles of the biopsy. LymphAreaRatio1 is the Area Ratio calculated based on division of area covered by lymphocytes and tissue area. |
| 15 | Average of MyoAreaRatio1 | Average of all MyoAreaRatio1 on all tiles of the biopsy. MyoAreaRatio1 is the ratio of foci area in myocardium divided by area of myocardium. |
| 16 | Sum of MyoFociArea | Sum of foci area in myocardium. |
| 17 | Average of MyoFociAreaRatio4 | Average of all MyoFociAreaRatio4 on all tiles of the biopsy. MyoFociAreaRatio4 is the ratio of foci area in myocardium divided by area of the tile. |
| 18 | Sum of FociArea | Sum of lymphocyte foci area in whole specimen. |
| 19 | Sum of MyoFociAreaRatio4 | Sum of all MyoFociAreaRatio4 on all tiles of the biopsy. MyoFociAreaRatio4 is the ratio of foci area in myocardium divided by area of the tile. |
| 20 | Average of FociAreaRatio1 | Average of all FociAreaRatio1 on all tiles of the biopsy. FociAreaRatio1 is the FociArea divided by area of the tile. |

Figure 12:
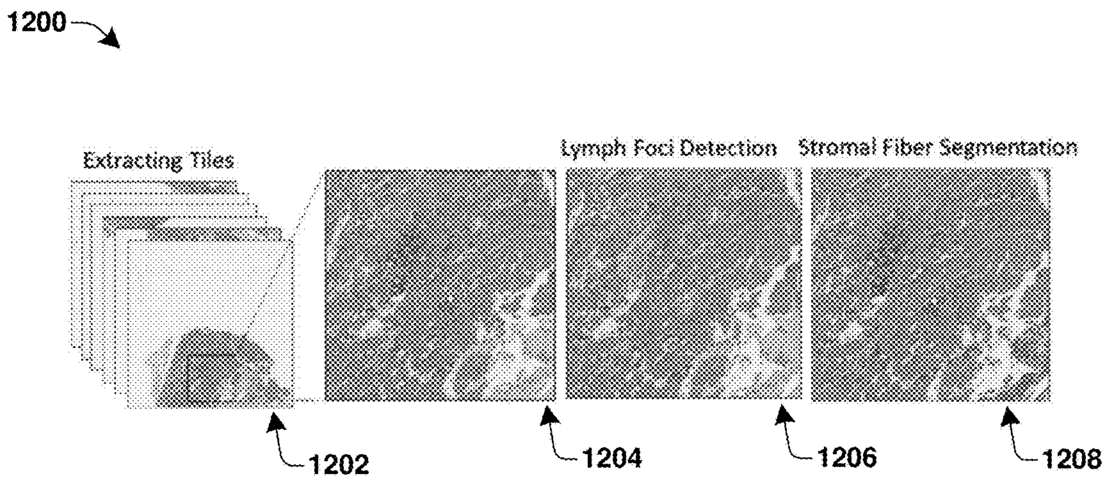
FIG. 12 illustrates some embodiments of images corresponding to a work flow of a segmentation method for identify lymphocyte foci within a disclosed machine learning pipeline.

FIG. 12 illustrates some embodiments of digitized images corresponding to a work flow 1200 of a segmentation method for identify lymphocyte foci within a disclosed machine learning pipeline.

As shown in work flow 1200, the plurality of tiles 1202 may respectively be segmented to identify a region of interest 1204. In some embodiments, within the region of interest, lymphocyte foci may be identified (as shown in image 1206). In some embodiments, within the region of interest stromal fibers may also be identified (shown in image 1208).

Figure 13A:
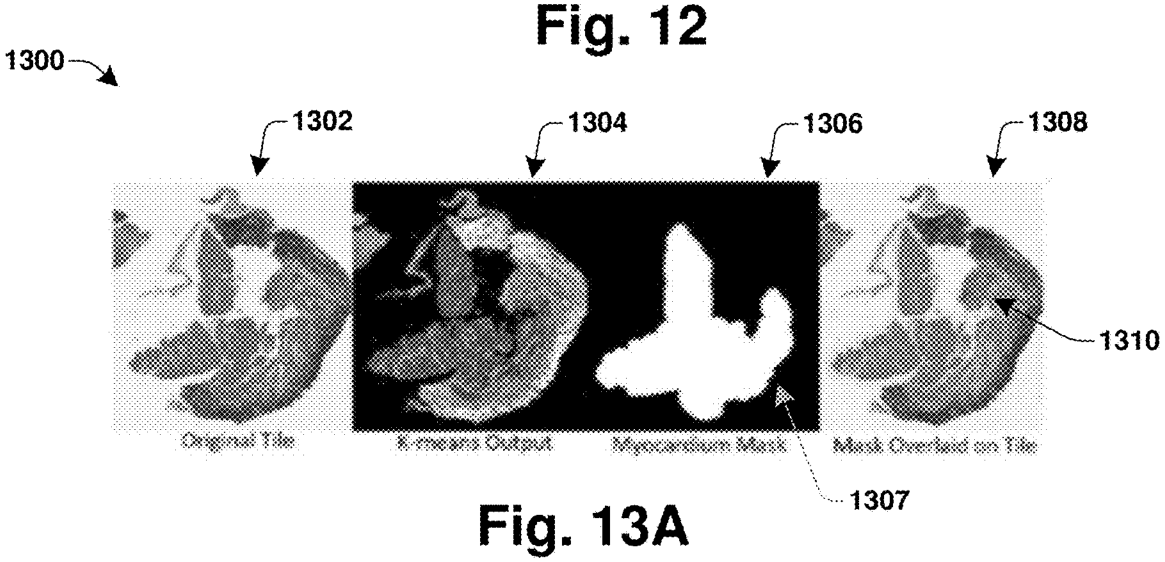
FIGS. 13A-13B illustrate some embodiments of images corresponding to exemplary work flows for lymphocyte foci identification as provided in a disclosed machine learning pipeline.

FIG. 13A illustrates some embodiments of digitized images corresponding to a workflow 1300 of a segmentation method for generating a myocardium mask within a disclosed machine learning pipeline.

As shown in workflow 1300, a digitized EMB image 1302 from a clinical histology slide stained with H&E is shown. A K-means segmentation segments the digitized EMB image 1304 into myocytes (shown in dark gray), interstitium/stroma (shown in light grey), and non-myocyte nuclei (shown in white). A myocardium mask 1306 may be formed from the myocyte segmentation (shown in digitized EMB image 1304) to identify a myocardial compartment 1307. The myocardium mask 1306 may be over laid with the digitized EMB image 1302 to generate a digitized EMB image 1308 that enables independent analysis of lymphocytes within a myocardial compartment 1310 and within an endocardial compartment. In some embodiments, the plurality of histological features may comprise a number, density, and/or area of lymphocyte foci within a myocardial compartment, while ignoring lymphocyte foci within an endocardial compartment (e.g., to avoid considering guilty lesions as lymphocyte foci).

Figure 13B:
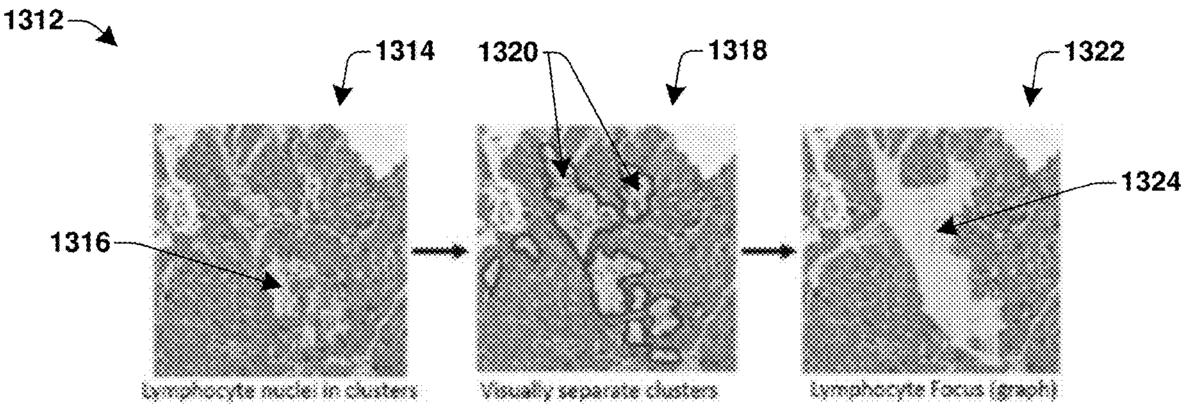

FIG. 13B illustrates some embodiments of digitized images corresponding to a workflow 1312 of a segmentation method for lymphocyte foci identification as provided in a disclosed machine learning pipeline.

As shown in workflow 1312, a digitized EMB image 1314 from a clinical histology slide stained with H&E is shown. Within the digitized EMB image 1314, lymphocytes may be identified as clustering together via area thresholding of individual lymphocyte nuclei. For example, the overlay of individual lymphocytes 1316 is shown as a cluster. As shown in image 1318, based upon the overlay of individual lymphocytes, distinct lymphocyte clusters 1320 can be identified. As shown in image 1322, proximity graph thresholding may be applied to the distinct lymphocyte clusters 1320 to merge nearby distinct lymphocyte clusters 1320 into a common lymphocyte focus 1324 for reproducing foci counting as outlined by the ISHL grading scheme.

Figure 14:
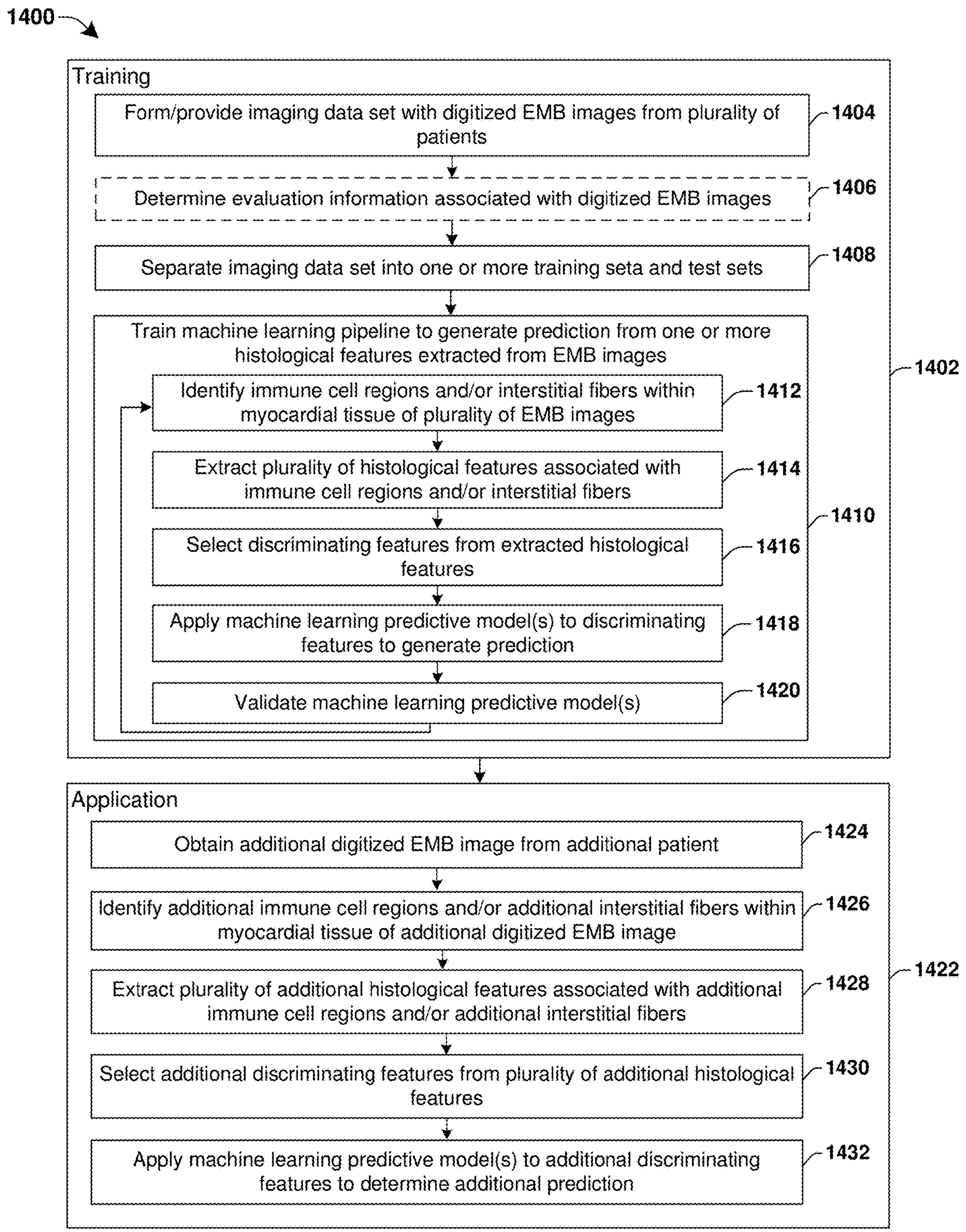
FIG. 14 illustrates some embodiments of a block diagram corresponding to a method of generating and applying a machine learning pipeline to determine a prediction for a transplant recipient based on histological features extracted from digitized EMB images.

FIG. 14 illustrates some additional embodiments of a method 1400 of generating a machine learning pipeline that is configured to determine a prediction of patients having had a heart transplant and applying the machine learning pipeline to an additional patient.

The method 1400 comprises a training phase 1402 and an application phase 1422. The training phase 1402 is configured to generate a machine learning pipeline that is able to provide a prediction of a patient that has received a heart transplant by using one or more histological feature extracted from digitized EMB images of the patient. In some embodiments, the training phase 1402 may be performed according to acts 1404-1212.

At act 1404, an imaging data set is provided and/or formed to comprise a plurality of digitized EMB images from a plurality of patients having had a heart transplant.

At act 1406, evaluation information associated with the plurality of digitized EMB images may be determined, in some embodiments.

At act 1408, the plurality of digitized EMB images within the imaging data set are separated into one or more training sets and one or more test sets. In some embodiments, the machine learning model may break the plurality of digitized EMB images into k folds of data.

At act 1410, a machine learning pipeline is trained to generate a prediction from histological features extracted from the plurality of digitized EMB images. In some embodiments, the machine learning pipeline may operate on k−1 folds for training and the remaining 1 fold (e.g., the kth fold) for testing over a plurality of iterations (e.g., over 500 iterations). In some embodiments, each of the iterations may perform one or more operations of acts 1412-1420.

At act 1412, immune cell regions (e.g., lymphocyte foci) and/or interstitial fibers are identified within myocardial tissue of the plurality of digitized EMB images within the one or more training sets or the one or more test sets.

At act 1414, a plurality of histological features associated with the immune cell regions and/or interstitial fibers are extracted.

At act 1416, a subset of the plurality of histological features are selected as discriminating features.

At act 1418, one or more predictive machine learning models are trained using the discriminating features.

At act 1420, the one or more predictive machine learning models are validated. In some embodiments, the evaluation information associated with the plurality of digitized EMB images may be used to validate the one or more predictive machine learning models.

The application phase 1422 is configured to utilize the machine learning pipeline on one or more additional images, which are taken from an additional patient having had a heart transplant, to determine a prediction of the additional patient.

At act 1424, an additional digitized EMB image is obtained from an additional patient. The additional patient has received a transplanted heart.

At act 1426, additional immune cell regions (e.g., lymphocyte clusters and/or foci) and/or additional interstitial fibers are identified within myocardial tissue of the additional digitized EMB image.

At act 1428, a plurality of additional histological features associated with the additional immune cell regions and/or additional interstitial fibers are extracted.

At act 1430, a subset of the plurality of additional histological features are selected as additional discriminating features.

At act 1432, one or more machine learning predictive models are applied to the additional discriminating features to generate an additional prediction of the additional patient. Based on the additional prediction, a therapeutic treatment (e.g., antirejection or immunosuppressant medications, intravenous steroids, plasmapheresis, a new heart transplant, or the like) may be selected for the additional patient and applied by a health care professional to try to avoid rejection of the transplanted heart.

Figure 15:
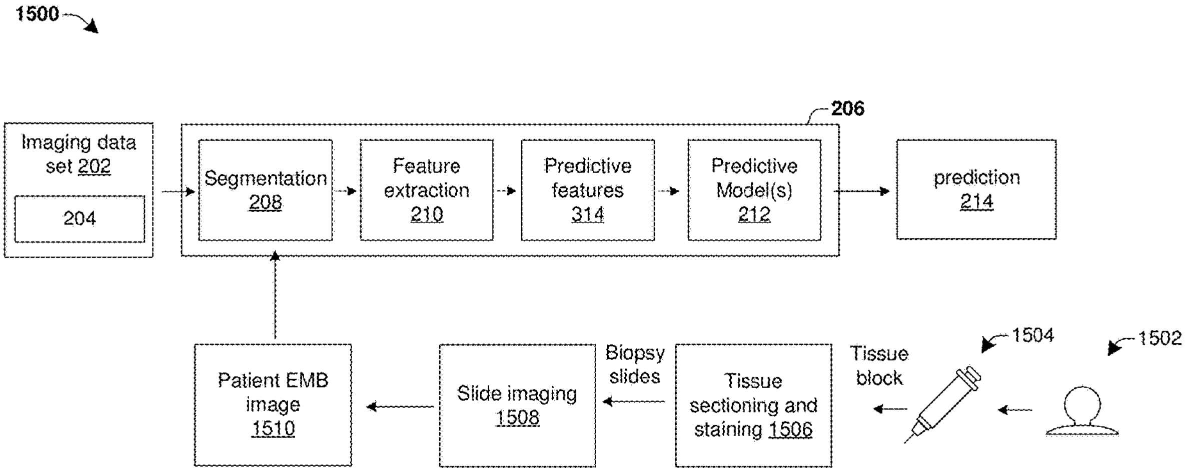
FIG. 15 illustrates some embodiments of a machine learning pipeline configured to determine a prediction for a transplant recipient based on histological features extracted from digitized EMB images.

FIG. 15 illustrates some embodiments of a block diagram 1500 of a machine learning pipeline configured to determine a prediction for a transplant recipient based on histological features extracted from digitized EMB images.

As shown in the block diagram 1500, an imaging data set 202 is formed and/or provided. The imaging data set 202 comprises a plurality of digitized EMB images 204 are provided to a machine learning pipeline 206 that is configured to apply one or more predictive model(s) to histological features extracted from the plurality of digitized EMB images 204 to determine a prediction 214 of a patient having had a heart transplant. In some embodiments, the machine learning pipeline 206 comprises a segmentation stage 208, a histological feature extraction stage 210, a predictive feature extraction stage 314, and a machine learning predictive model stage 212.

The segmentation stage 208 is configured to segment the plurality of digitized EMB images 204. In some embodiments, the segmentation stage 208 may be configured to identify immune cell regions (e.g., lymphocyte clusters and/or foci) within the plurality of digitized EMB images 204 and/or to identify interstitial fibers within the plurality of digitized EMB images 204. The histological feature extraction stage 210 is configured to extract a plurality of histological features from the immune cell regions and/or the interstitial fibers within respective ones of the plurality of digitized EMB images 204. The predictive feature extraction stage 314 is configured to identify a set of discriminant features from the plurality of histological features. The machine learning predictive model stage 212 is configured to apply and/or generate one or more machine learning predictive models that utilize the plurality of histological features to generate a prediction 214 of a patient.

Once the one or more machine learning predictive models are trained, they may be applied to an additional patient 1502 to generate a prediction for the additional patient 1502. In some embodiments, a biopsy 1504 may be performed on the additional patient 1502. In some embodiments, the biopsy 1504 may be performed by inserting a catheter into a heart of the additional patient 1502 to obtain a tissue sample (e.g., a tissue block). The tissue sample is the provided to a tissue sectioning tool 1506 that is configured to slice the tissue into thin slices that are placed on transparent slides (e.g., glass slides) to generate biopsy slides. The biopsy slides are subsequently provided to a slide imaging element 1508 (e.g., a photodetector) configured to convert the biopsy slides to the one or more additional digitized EMB images 1510.

The one or more additional digitized EMB images 1510 are provided to the machine learning pipeline 206, which is configured to segment the one or more additional digitized EMB images 1510, extract a second plurality of histological features from the segmented images, to select a subset of the second plurality of histological features as discriminant features, and to generate a prediction for the additional patient 1502 from the discriminant features.

Figure 16:
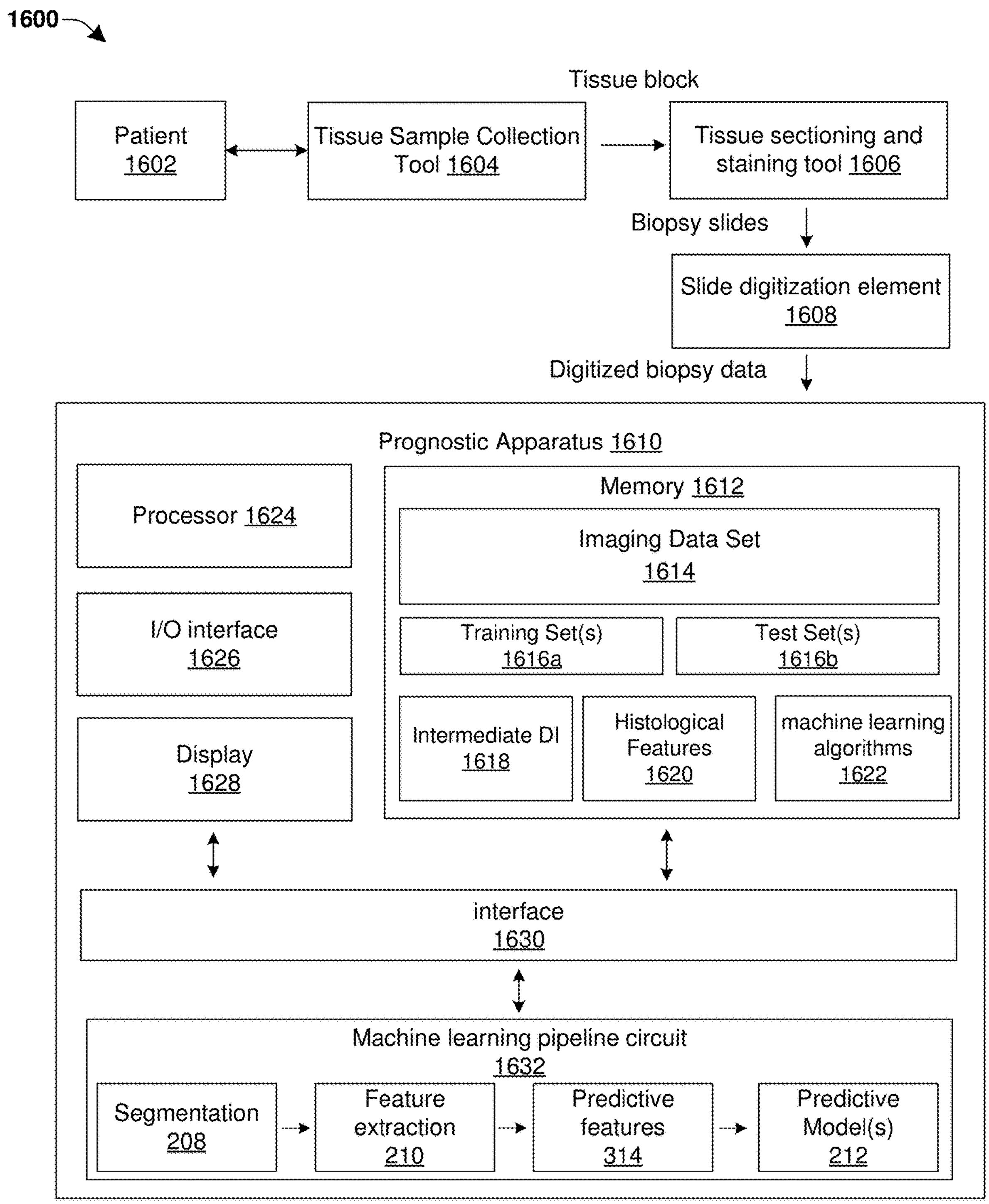
FIG. 16 illustrates some embodiments of a block diagram of an apparatus configured to determine a prediction for a transplant recipient based on histological features extracted from digitized EMB images.

FIG. 16 illustrates some embodiments of a block diagram of an apparatus 1600 configured to determine a prediction for a transplant recipient based on histological features extracted from digitized EMB images.

The apparatus 1600 comprises a prognostic apparatus 1610. The prognostic apparatus 1610 is coupled to a slide digitization element 1608 that is configured to obtain digitized images (e.g., whole slide images) of tissue samples collected from a patient 1602 having had a heart transplant. In some embodiments, one or more tissue samples (e.g., a tissue block) may be obtained using a tissue sample collection tool 1604 (e.g., a cannular, forceps, needle, punch, or the like). The one or more tissue samples may be provided to a tissue sectioning and staining tool 1606. In some embodiments, the tissue sectioning and staining tool 1606 may be configured to slice the one or more tissue samples into thin slices that are placed on transparent slides (e.g., glass slides) to generate biopsy slides. The tissue on the biopsy slides is then stained by applying a dye. The dye may be applied on the posterior and anterior border of the sample tissues to locate the diseased or tumorous cells or other pathological cells. In some embodiments, the biopsy slides may comprise H&E (Hematoxylin and Eosin) stained slides. The slide digitization element 1608 is configured to convert the biopsy slides to digitized biopsy data (e.g., whole slide images). In some embodiments, the slide digitization element 1608 may comprise an image sensor (e.g., a photodiode, CMOS image sensor, or the like) that is configured to capture a digital image of the biopsy slides.

The prognostic apparatus 1610 comprises a processor 1624 and a memory 1612. The processor 1624 can, in various embodiments, comprise circuitry such as, but not limited to, one or more single-core or multi-core processors. The processor 1624 can include any combination of general-purpose processors and dedicated processors (e.g., graphics processors, application processors, etc.). The processor(s) 1624 can be coupled with and/or can comprise memory (e.g., memory 1612) or storage and can be configured to execute instructions stored in the memory 1612 or storage to enable various apparatus, applications, or operating systems to perform operations and/or methods discussed herein.

The memory 1612 can be configured to store an imaging data set 1614 comprising digitized EMB images. The digitized EMB images may comprise digitized biopsy images having a plurality of pixels, each pixel having an associated intensity. In some additional embodiments, the digitized EMB images may be stored in the memory 1612 as one or more training sets **1616*a* of digitized images for training a classifier and/or one or more test sets 1616*b*** (e.g., validation sets) of digitized images.

The prognostic apparatus 1610 also comprises an input/output (I/O) interface 1626 (e.g., associated with one or more I/O devices), a display 1628, a machine learning pipeline circuit 1632, and an interface 1630 that connects the processor 1624, the memory 1612, the I/O interface 1626, and the machine learning pipeline circuit 1632. The I/O interface 1626 can be configured to transfer data between the memory 1612, the processor 1624, the machine learning pipeline circuit 1632, and external devices, for example, the slide digitization element 1608. The display 1628 is configured to output or display the prediction the prognostic apparatus 1610.

In some embodiments, the machine learning pipeline circuit 1632 may comprise a segmentation stage 208, a histological feature extraction stage 210, a predictive feature extraction stage 314, and a machine learning predictive model stage 212. In some embodiments, the segmentation stage 208 is configured to segment the plurality of digitized EMB images 204 to identify immune cell regions (e.g., lymphocyte clusters and/or foci) and/or interstitial fibers (e.g., collagen fibers, stromal fibers, or the like) within the plurality of digitized EMB images 204. In some embodiments, the histological feature extraction stage 210 is configured to extract a plurality of histological features 1620 from the immune cell regions and/or interstitial fibers within respective ones of the plurality of digitized EMB images 204. The machine learning predictive model stage 212 is configured to apply and/or generate one or more machine learning predictive models that utilize the plurality of histological features 1620 to generate a prediction 214 of a patient.

In some embodiments, the segmented images may be stored in the memory 1612 as intermediate digitized images 1618. In some embodiments, the digitized EMB images may be broken into tiles, which may be stored in the memory as intermediate digitized images 1618.

In some embodiments, the machine learning pipeline circuit 1632 may operate according to machine learning algorithms 1622 stored in memory 1612. The machine learning algorithms 1622 may comprise algorithms that are configured to generate a prediction comprising a grade associated with one or more digitized EMB images (e.g., a binary grade, a 4-grade classification, etc.). In other embodiments, the machine learning algorithms 1622 may comprise algorithms that are configured to generate a prediction comprising a clinical trajectory.

Example Use Case 1

The following discussion provides example embodiments in connection with a first example use case involving a method of determining a clinical trajectory of a transplant recipient based on morphological features extracted from endomyocardial biopsy (EMB) images.

Introduction

Cellular rejection occurs in 20-40% of transplant recipients with an increased risk of graft failure. Previously, we developed a model for predicting ISHLT rejection grades via the automated extraction of morphologic features in Endomyocardial biopsy (EMB) images. Considering the frequent discordance between conventional rejection grade and clinical rejection severity, in this work, we sought to identify morphologic features that predict the clinical trajectory of rejection events.

Method

Our study comprised 299 EMBs with grade and trajectory labels. Trajectory labels are based on the development of overt clinical signs of allograft injury as "clinically evident" or "clinically silent". Morphologic features describing number, spatial arrangement of lymphocytes, and shape, density, and/or orientation of interstitial fibers were computationally extracted. To identify the top features associated with clinically evident disease, the T-test method was applied across 500 iterations of 3-fold cross validation. In each iteration, a quadratic discriminant analysis model was trained with top 10 features on 2 folds of data set using trajectory labels ($M_{trj}$) and was validated on one hold out test set. This model was trained using grade labels ($M_{grd}$) to predict "high" (2R+3R) or "low" (0R+1R). To assess feature importance, in each model, the frequency of every feature appearing in the classifier was measured through iterations.

Results

The mean area under the receiver operating curve of $M_{trj}$ and $M_{grd}$ was 0.80±0.04 and 0.84±0.02 correspondingly. The top features for predicting grades differ substantially from those for predicting clinical trajectory (FIG. 4).

Conclusions

The additional features required to predict clinical trajectory vs. rejection grade may explain the discordance between conventional histology and rejection syndrome observed in clinical practice, and highlights the translational potential of computer-assisted histologic analysis of EMBs.

Example Use Case 2

The following discussion provides example embodiments in connection with a second example use case involving a method of determining a clinical trajectory of a transplant recipient based on morphological features extracted from endomyocardial biopsy (EMB) images.

Introduction

Cardiac allograft rejection is a serious concern, occurring in 30-40% of patients in the first-year post-transplant and increase risk of graft failure. The international society for heart and lung transplantation (ISHLT) has recommended surveillance via endomyocardial biopsy (EMB) with standardized histologic grading since 1990. Unfortunately, inter-rater agreement between pathologists using the ISHLT grading framework is quite poor, with an approximate absolute agreement of 70% and a Cohen's Kappa statistic of 0.39. So, a machine learning approach providing accurate, highly reproducible, and easily disseminated grading offers distinct advantages over the current standard of care.

Method

Our study comprised 1109 digitally scanned biopsy images from n=410 heart transplant patients with histologic grading between 0R (no rejection) and 3R (severe rejection). For each slide, lymphocyte foci located within myocardium tissue were identified and 127 image features relating to the number and arrangement of machine detected lymphocytes foci were extracted (see FIG. 1 bottom). This approach aids in the prevention of foci over-counting.

Results

A training set of 302 patients (790 EMBs) was employed to identify the top 80 of 127 extracted features using Minimum Redundancy Maximum Relevance (mRMR). A Random forest classifier was then trained in conjunction with these 80 features to predict rejection grade and subsequently evaluated on the remaining 108 patients (319 EMBs). The classifier was able to differentiate low (0R and 1R) versus high (2R and 3R) rejection grades with an area under the receiver operating characteristic curve (AUC) of 0.98. Additionally, the classifier yielded an accuracy of 0.72 in identifying individual grades.

Conclusions

Quantitative features derived from lymphocyte foci on routine EMBs appear to (1) distinguish low from high grade rejection cases, and (2) determine individual rejection grades of heart transplant patients.

Example Use Case 3

The following discussion provides example embodiments in connection with a third example use case involving a method of determining a clinical trajectory of a transplant recipient based on morphological features extracted from endomyocardial biopsy (EMB) images.

Purpose

It has long been recognized that transplanted hearts develop a stiffened, restrictive physiology at an accelerated rate compared to native hearts. While this is thought to be due to a variety of factors which result in local inflammatory injury and subsequent remodeling. Inflammatory insults and their subsequent effects on in-situ tissue architecture have never been rigorously studied. In this work, we sought to use quantitative image analysis tools to measure a variety of morphologic biomarkers pertaining to collagen changes in a large cohort of endomyocardial biopsy (EMB) samples. We then apply these features to investigate the roles of several potential causes of inflammation (reperfusion injury, guilty lesions, and a history of cellular rejection) in the transplanted heart.

Method

Given that the collagen in different regions have different responses to the causes of inflammation, a U-net model was trained to classify collagen into three types according to its location: collagen at the edge of the myocardium, collagen around myocytes, and collagen inside stroma. Collagen fibers were further segmented by utilizing a local binary pattern operator combined with OTSU algorithm. We then extracted a set of 216 biologically-inspired collagen features, relating to the density, morphology, spatial arrangement and interaction with myocytes. The relationship between 216 collagen features and the causes of inflammation were comparatively analyzed. Feature selection was employed to identify the most 5 predictive features on a set of 911 slides and these were subsequently trained with a random forest classifier to predict the existence of the causes of inflammation. The area under the receiver operating characteristic curves (AUCs) were calculated to evaluate the model performance on the test 395 slides.

Results

1) The AUCs for predicting the existence of reperfusion injury, guilty lesions, and a history of cellular rejection reached 0.65, 0.61 and 0.81, respectively. This showed that collagen features were strongly linked to the causes of inflammation studied. 2) Different causes of inflammation showed different effects on the three types of collagen; guilty lesion mainly acted on the collagen at the edge of the myocardium, while reperfusion injury mainly acted on the collagen around myocytes. 3) Collagen features were more closely related to the historical rejection grade than the current rejection grade, indicating that the change of collagen features was a gradual accumulation process.

Conclusions

This work demonstrates that the novel biomarkers derived from collagen are highly potential for the mechanism-exploring of the causes of inflammation in remodeling of the transplanted myocardium.

Therefore, in some embodiments the present disclosure relates to a non-transitory computer-readable medium storing computer-executable instructions that, when executed, cause a processor to perform operations. The operations including obtaining one or more digitized endomyocardial biopsy (EMB) images from a patient having had a heart transplant; extracting a plurality of histological features from the one or more digitized EMB images; and applying a machine learning predictive model to operate on the plurality of histological features to generate a prediction for the patient, the prediction including a grade or a clinical trajectory associated with the patient.

In other embodiments, the present disclosure relates to a method determining a prediction associated with a transplant patient. The method includes identifying one or more immune cell regions or one or more interstitial fibers of one or more digitized endomyocardial biopsy (EMB) images from one or more patients; generating a plurality of histological features associated with the one or more immune cell regions or the one or more interstitial fibers; determining a set of discriminant features from the plurality of histological features, the set of discriminant features being a subset of the plurality of histological features that are highly determinative of a prediction; and operating a machine learning predictive model on the set of discriminant features to generate the prediction.

In yet other embodiments, the present disclosure relates to an apparatus configured to generate a prediction associated with a transplant patient. The apparatus includes a memory configured to store an imaging data set comprising one or more digitized endomyocardial biopsy (EMB) images from one or more patients; and a machine learning pipeline. The machine learning pipeline includes a segmentation stage configured to identify one or more immune cell regions or one or more interstitial fibers within the one or more digitized EMB images; a feature extraction stage configured to extract a plurality of histological features associated with the one or more immune cell regions or the one or more interstitial fibers; and a machine learning predictive model configured to operate on the plurality of histological features to generate one or more predictions for the one or more patients.

Examples herein can include subject matter such as an apparatus, including a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system according to embodiments and examples described.

References to "one embodiment", "an embodiment", "one example", and "an example" indicate that the embodiment (s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action (s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:

obtaining one or more digitized endomyocardial biopsy (EMB) images from a patient having had a heart transplant;

identifying one or more lymphocyte clusters within the one or more digitized EMB images;

applying proximity graph thresholding to the one or more lymphocyte clusters to merge nearby ones of the one or more lymphocyte clusters into a lymphocyte focus;

extracting a plurality of histological features from the one or more digitized EMB images; and applying a machine learning predictive model to operate on the plurality of histological features to generate a prediction for the patient, wherein the prediction comprises a grade or a clinical trajectory associated with the patient.

2. The non-transitory computer-readable medium of claim 1, further comprising:

identifying one or more immune cell regions or more interstitial fibers within myocardial tissue of the one or more digitized EMB images, wherein the plurality of histological features are associated with the one or more immune cell regions or the one or more interstitial fibers, wherein the one or more immune cell regions comprise one or more of lymphocytes, lymphocyte foci, and the one or more lymphocyte clusters.

3. The non-transitory computer-readable medium of claim 1, wherein the plurality of histological features comprise one or more of a number of lymphocytes, a spatial arrangement of lymphocytes, a shape of one or more interstitial fibers, and an orientation of the one or more interstitial fibers.

4. The non-transitory computer-readable medium of claim 1, wherein the plurality of histological features comprise one or more of:

features quantifying a number of lymphocyte foci in different tissue compartments;

size or density statistics for the one or more lymphocyte clusters; and spatial or edge interactions of the one or more lymphocyte clusters or lymphocyte foci.

5. The non-transitory computer-readable medium of claim 1, wherein the machine learning predictive model is configured to use a support vector machine (SVM) classification method.

6. The non-transitory computer-readable medium of claim 1, wherein the machine learning predictive model comprises a quadratic discriminant analysis model.

7. The non-transitory computer-readable medium of claim 1, further comprising:

providing trajectory labels for the one or more digitized EMB images, wherein the trajectory labels describe clinical outcomes of the patient associated with one or more digitized EMB images; and utilizing the trajectory labels to validate the prediction.

8. The non-transitory computer-readable medium of claim 1, wherein the plurality of histological features relate to interstitial stromal fibers.

9. The non-transitory computer-readable medium of claim 1, wherein the plurality of histological features are associated with lymphocytes in a myocardial compartment and not with lymphocytes within an endocardial compartment.

10. The non-transitory computer-readable medium of claim 1, further comprising:

obtaining an additional digitized EMB image of an additional patient;

segmenting the additional digitized EMB image to identify one or more additional immune cell regions or one or more additional interstitial fibers;

extracting a plurality of additional histological features from the one or more additional immune cell regions or the one or more additional interstitial fibers; and applying the machine learning predictive model to the plurality of additional histological features to determine an additional prediction of the additional patient.

11. The non-transitory computer-readable medium of claim 1, wherein the prediction comprises the grade associated with the patient, wherein the grade comprises a binary classification indicative of a rejection of the heart transplant of the patient.

* * * * *